US 9,279,819 B2

(12) United States Patent
Mizumoto et al.

(10) Patent No.: US 9,279,819 B2
(45) Date of Patent: Mar. 8, 2016

(54) SAMPLE PROCESSING SYSTEM, METHOD FOR SAVING ELECTRICITY CONSUMED BY SAMPLE PROCESSING SYSTEM, AND NON-TRANSITORY STORAGE MEDIUM

(75) Inventors: Toru Mizumoto, Kobe (JP); Akio Toyoda, Kobe (JP)

(73) Assignee: SYSMEX CORPORATION, Kobe-Shi, Hyogo (JP)

(*) Notice: Subject to any disclaimer, the term of this patent is extended or adjusted under 35 U.S.C. 154(b) by 686 days.

(21) Appl. No.: 12/871,613

(22) Filed: Aug. 30, 2010

(65) Prior Publication Data
US 2011/0054800 A1 Mar. 3, 2011

(30) Foreign Application Priority Data
Aug. 31, 2009 (JP) ................................. 2009-199613

(51) Int. Cl.
*G01N 35/00* (2006.01)
*G01N 35/04* (2006.01)

(52) U.S. Cl.
CPC .... *G01N 35/00584* (2013.01); *G01N 35/00603* (2013.01); *G01N 2035/00326* (2013.01); *G01N 2035/0415* (2013.01)

(58) Field of Classification Search
CPC .................... G01N 35/0092; G01N 35/00584; G01N 2035/00326; G01N 35/00603; G01N 33/48785
USPC .......................................................... 702/21
See application file for complete search history.

(56) References Cited

U.S. PATENT DOCUMENTS

| | | | |
|---|---|---|---|
| 5,209,903 A * | 5/1993 | Kanamori et al. ............... 422/65 |
| 2002/0098117 A1* | 7/2002 | Ammann et al. ................ 422/64 |
| 2003/0117161 A1* | 6/2003 | Burns ................. G01R 31/2851 |
| | | | 324/750.02 |
| 2003/0149929 A1* | 8/2003 | White ............................ 714/766 |
| 2004/0023404 A1 | 2/2004 | Shibata |
| 2006/0203226 A1* | 9/2006 | Roche et al. ..................... 356/39 |
| 2006/0216199 A1* | 9/2006 | Koike .............................. 422/65 |
| 2008/0310999 A1 | 12/2008 | Yagi et al. |
| 2009/0269799 A1* | 10/2009 | Winkelman et al. ............ 435/29 |

FOREIGN PATENT DOCUMENTS

| | | |
|---|---|---|
| EP | 2 040 081 A2 | 3/2009 |
| JP | H11-271309 A | 10/1999 |
| JP | 11-316236 A | 11/1999 |
| JP | 2003-121449 | 4/2003 |
| JP | 2004-226065 A | 8/2004 |
| JP | 2007-127583 A | 5/2007 |
| JP | 2007-316092 A | 12/2007 |
| JP | 2008-281454 A | 11/2008 |

* cited by examiner

*Primary Examiner* — Sujoy Kundu
*Assistant Examiner* — Liam R Casey
(74) *Attorney, Agent, or Firm* — Brinks Gilson & Lione

(57) ABSTRACT

A sample processing system is disclosed which includes at least one processor and at least one memory that stores programs executable collectively by the at least one processor. According to the stored programs, the at least one processor transports sample containers through a conveying path along which there are arranged at least one first module for testing of samples and at least one second module for processing of samples which have been tested by the at least one first module. The at least one second module is switchable between an active state and an inactive state. The at least one processor further obtains a determination result as to whether a sample which has been tested by the at least one first module is necessary to be processed by the at least one second module.

18 Claims, 13 Drawing Sheets

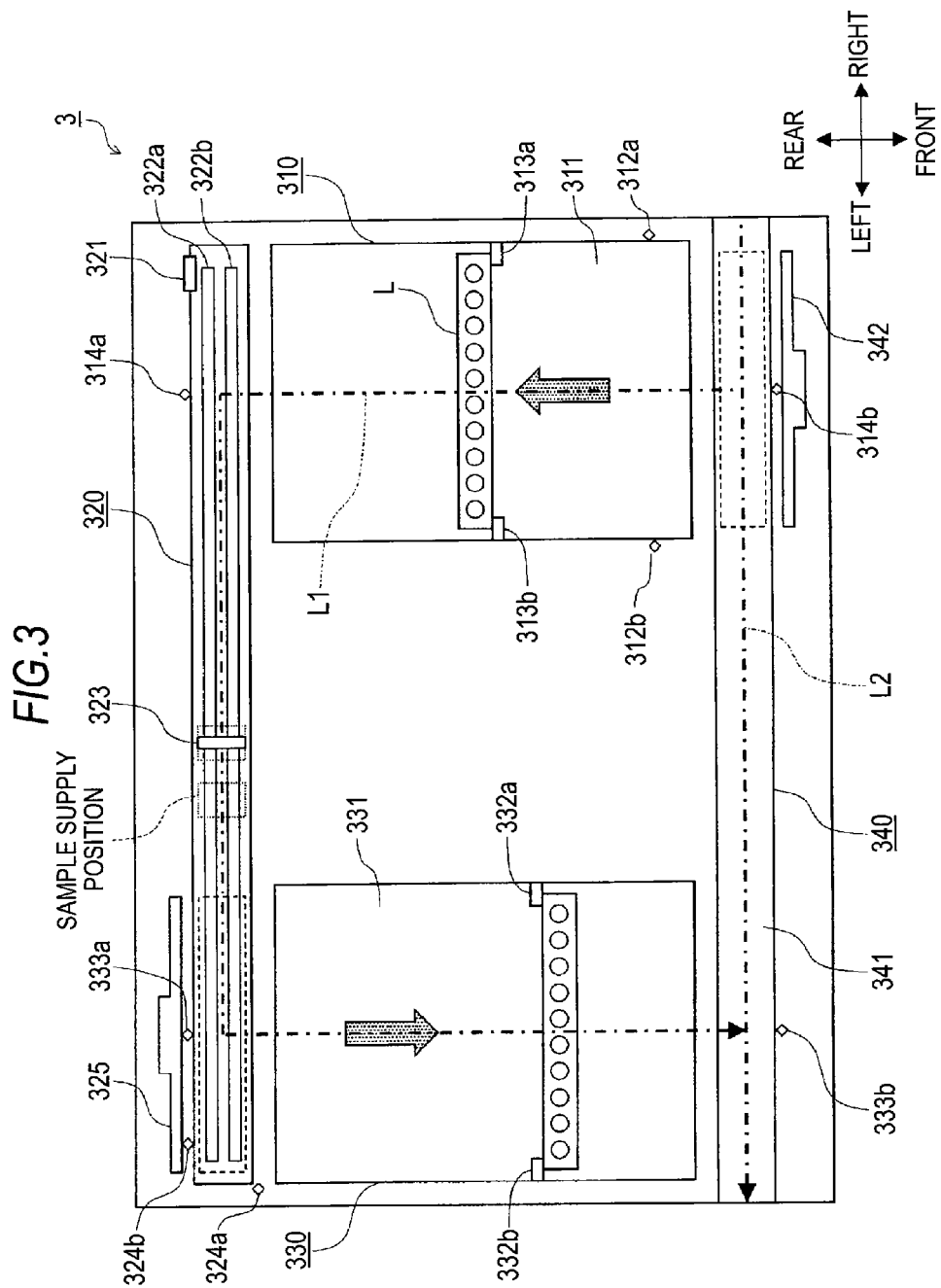

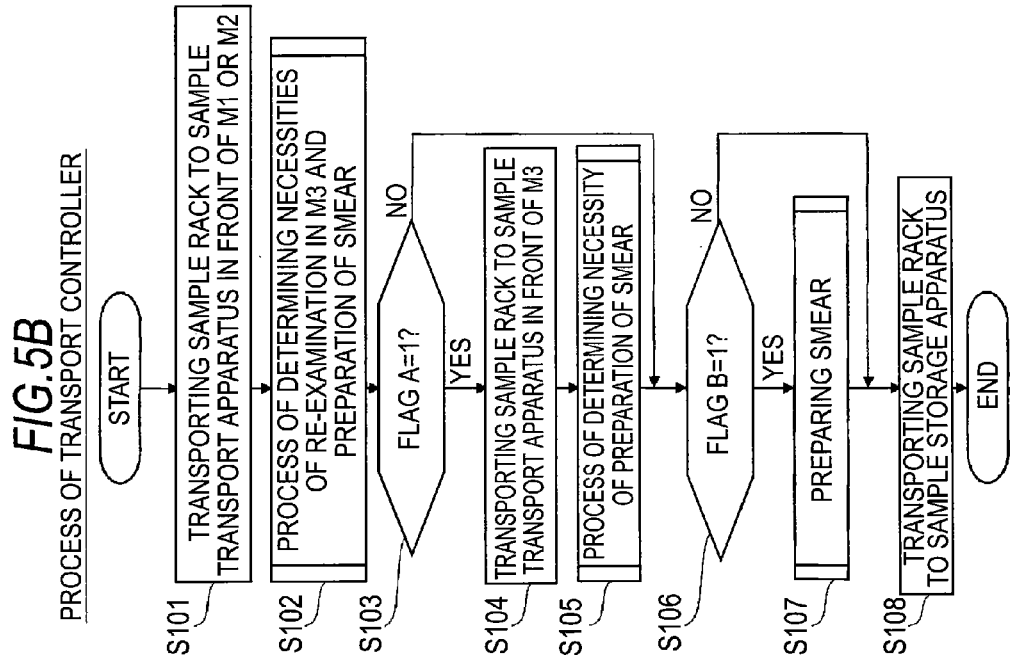
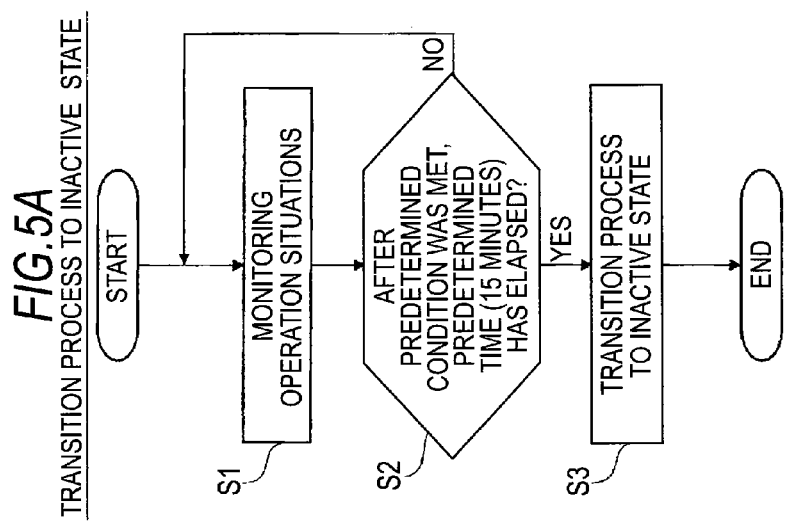

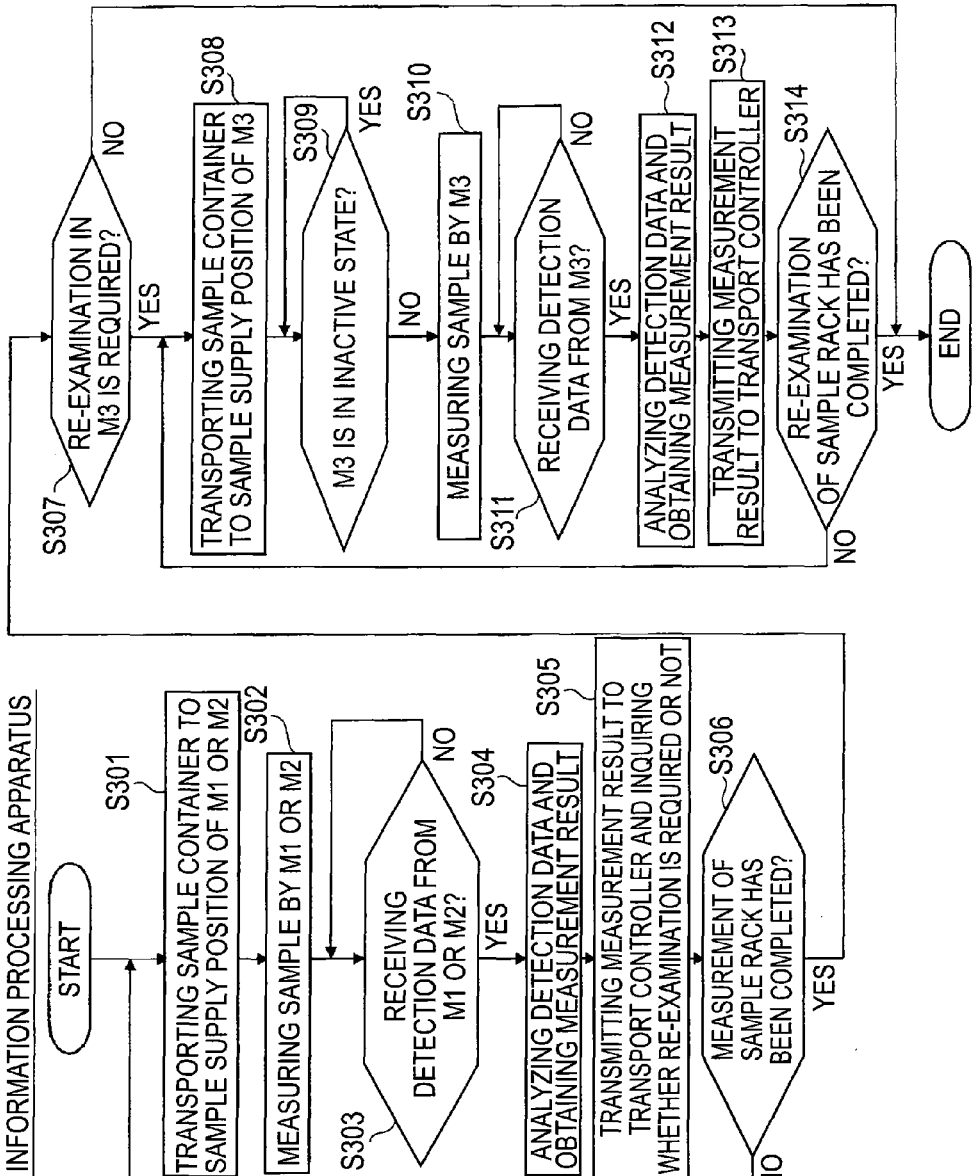

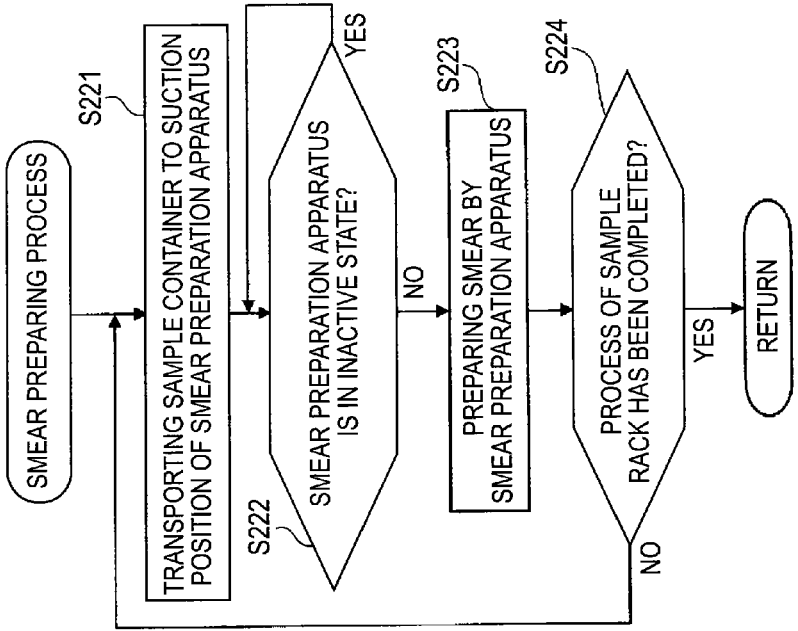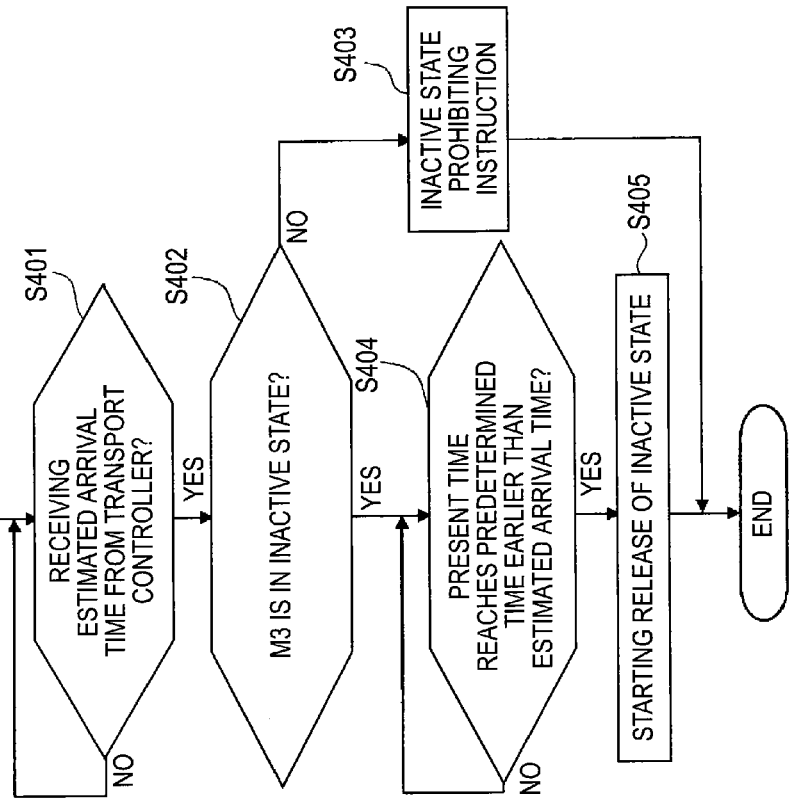

SAMPLE PROCESSING SYSTEM, METHOD FOR SAVING ELECTRICITY CONSUMED BY SAMPLE PROCESSING SYSTEM, AND NON-TRANSITORY STORAGE MEDIUM

RELATED APPLICATIONS

This application claims priority under 35 U.S.C. §119 to Japanese Patent Application No. 2009-199613 filed on Aug. 31, 2009, the entire content of which is hereby incorporated by reference.

TECHNICAL FIELD

The present invention relates to a sample processing system, method and non-transitory storage medium for performing a predetermined process such as examination or analysis on a sample such as blood.

BACKGROUND OF THE INVENTION

Sample processing apparatuses for processing a clinical sample such as blood or urine are used in medical institutions such as hospitals. Some of such sample processing apparatuses are composed of a plurality of analysis modules and a transport apparatus for transporting a sample to the plurality of analysis modules, so as to improve the sample processing capacity. In addition, some of such sample processing apparatuses are configured such that, when it is determined that the same sample is required to be re-examined as a result of the analysis (first examination) in one analysis module, the re-examination is automatically carried out in another module in the same apparatus (for example, see U.S. patent application publication No. 2008/0310999).

In addition, some of this type of sample processing apparatuses has a function of changing a state of the apparatus into an inactive state in order to suppress power consumption (for example, see Japanese laid-open patent publication No. 2003-121449).

In the sample processing apparatus which is configured so as to carry out the re-examination as in the above-mentioned U.S. patent application publication No. 2008/0310999, the usage frequency of an analysis module for use in the re-examination is smaller than that of another analysis module for carrying out first examination in many cases. Particularly, in a time period in which the number of samples is small, the time in which the analysis module for use in the re-examination is not used increases. However, even in this situation, the analysis module for use in the re-examination is made active so as to be able to promptly start the re-examination in the conventional sample processing apparatus. Accordingly, a problem occurs in that the power consumption increases.

In Japanese laid-open patent publication No. 2003-121449, it is disclosed a technique for suppressing the power consumption of an entire sample analysis system. However, it is not disclosed suppressing the power consumption of the analysis module for use in the re-examination.

SUMMARY OF THE INVENTION

The scope of the present invention is defined solely by the appended claims, and is not affected to any degree by the statements within this summary.

The present invention provides a first sample processing system. The first sample processing system embodying features of this invention comprises at least one processor and at least one memory that stores programs executable collectively by the at least one processor. According to the stored programs, the at least one processor transports sample containers through a conveying path along which there are arranged at least one first module for testing of samples and at least one second module for processing of samples which have been tested by the at least one first module. The at least one second module is switchable between an active state and an inactive state. The at least one processor also obtains a determination result as to whether a sample which has been tested by the at least one first module is necessary to be processed by the at least one second module. If the sample is determined necessary to be processed by the at least one second module, the at least one processor transports a sample container containing the sample to the at least one second module for processing. If the at least one second module is in the inactive state, the at least one processor places the at least one second module in the active state to make it ready to process the sample.

The present invention also provides a first method for saving electricity consumed by a sample processing system. The method embodying features of this invention comprises transporting sample containers through a conveying path along which there are arranged at least one first module for testing of samples and at least one second module for processing of samples which have been tested by the at least one first module, wherein the at least one second module is switchable between an active state and an inactive state. The method further comprises obtaining a determination result as to whether a sample which has been tested by the at least one first module is necessary to be processed by the at least one second module. If the sample is determined necessary to be processed by the at least one second module, transporting a sample container containing the sample to the at least one second module for processing. If the at least one second module is in the inactive state, placing the at least one second module in the active state to make it ready to process the sample.

The present invention further provides a first non-transitory storage medium. The storage medium embodying features of this invention stores programs executable collectively by at least one processor of a sample processing system. According to the stored program, the at least one processor transports sample containers through a conveying path along which there are arranged at least one first module for testing of samples and at least one second module for processing of samples which have been tested by the at least one first module. The at least one second module is switchable between an active state and an inactive state. The at least one processor obtains a determination result as to whether a sample which has been tested by the at least one first module is necessary to be processed by the at least one second module. If the sample is determined necessary to be processed by the at least one second module, the at least one processor transports a sample container containing the sample to the at least one second module for processing. If the at least one second module is in the inactive state, the at least one processor places the at least one second module in the active state to make it ready to process the sample.

The effect and meaning of the present invention will be further clear by descriptions of the following embodiments. However, the following embodiments are an example when the present invention is embodied, and the present invention is not limited by the following embodiments.

BRIEF DESCRIPTION OF THE DRAWINGS

FIG. 3 is a top view showing the configuration of a sample transport apparatus according to the first embodiment.

FIG. 5A is a flowchart showing a transition process to an inactive state according to the first embodiment.

FIG. 5B is a flowchart showing a process of the transport controller according to the first embodiment.

FIG. 7 is a flowchart showing a process of the information processing apparatus according to the first embodiment.

FIG. 8A is a flowchart showing an inactive state releasing process according to the first embodiment.

FIG. 8B is a flowchart showing the content of the process of S107 of FIG. 5B.

DETAILED DESCRIPTION OF THE PREFERRED EMBODIMENT

The present embodiment is a sample processing system for performing examination and analysis on blood, to which the present invention is applied. A sample processing system according to this embodiment includes three measuring units and one smear preparation apparatus. Blood analyses are performed in parallel by two of the three measuring units, and when re-examination is required on the basis of the analysis result, the remaining one measuring unit performs the measurement. When it is necessary to prepare a smear on the basis of the analysis result of the three measuring units, a smear is prepared by the smear preparation apparatus.

1. First Embodiment

Hereinafter, a sample processing apparatus according to a first embodiment will be described with reference to the drawings.

Figure 1:
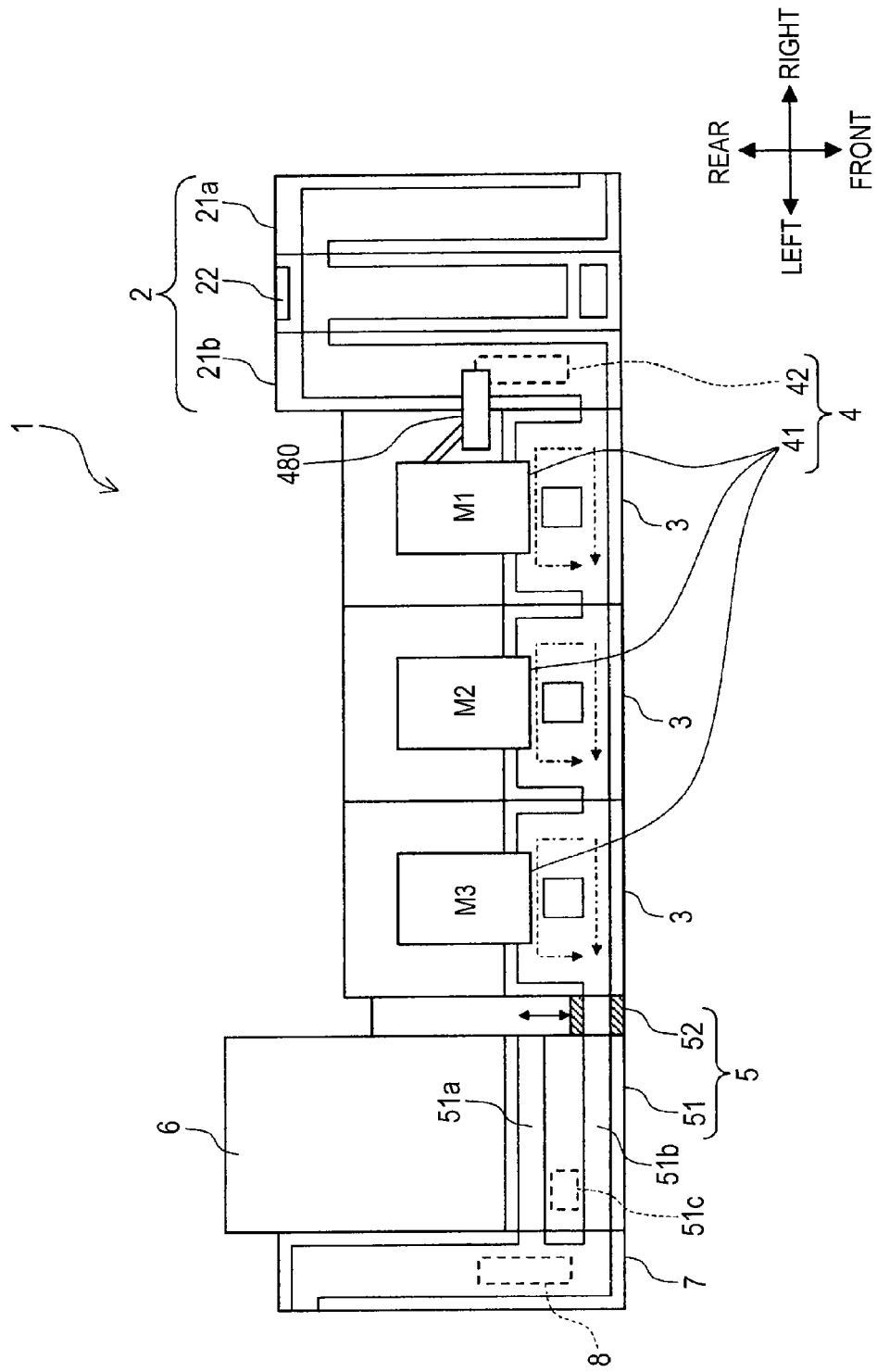
FIG. 1 is a diagram showing the configuration of a sample processing system according to a first embodiment.

FIG. 1 is a top view showing the configuration of a sample processing system 1, when viewed from the upper side. The sample processing system 1 according to this embodiment includes a sample input apparatus 2, three sample transport apparatuses 3, a blood cell analysis apparatus 4, a sample transport apparatus 5, a smear preparation apparatus 6, a sample storage apparatus 7 and a transport controller 8.

The sample input apparatus 2 includes two sample delivery units 21a and 21b and a bar-code reading unit 22 which is disposed between the two sample delivery units 21a and 21b. The sample delivery units 21a and 21b are configured such that a plurality of sample racks can be placed therein.

Figure 2A:
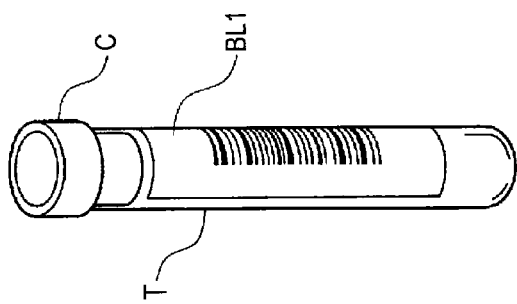
FIGS. 2A and 2B show perspective views showing the appearances of a sample container and a sample rack.
Figure 2B:
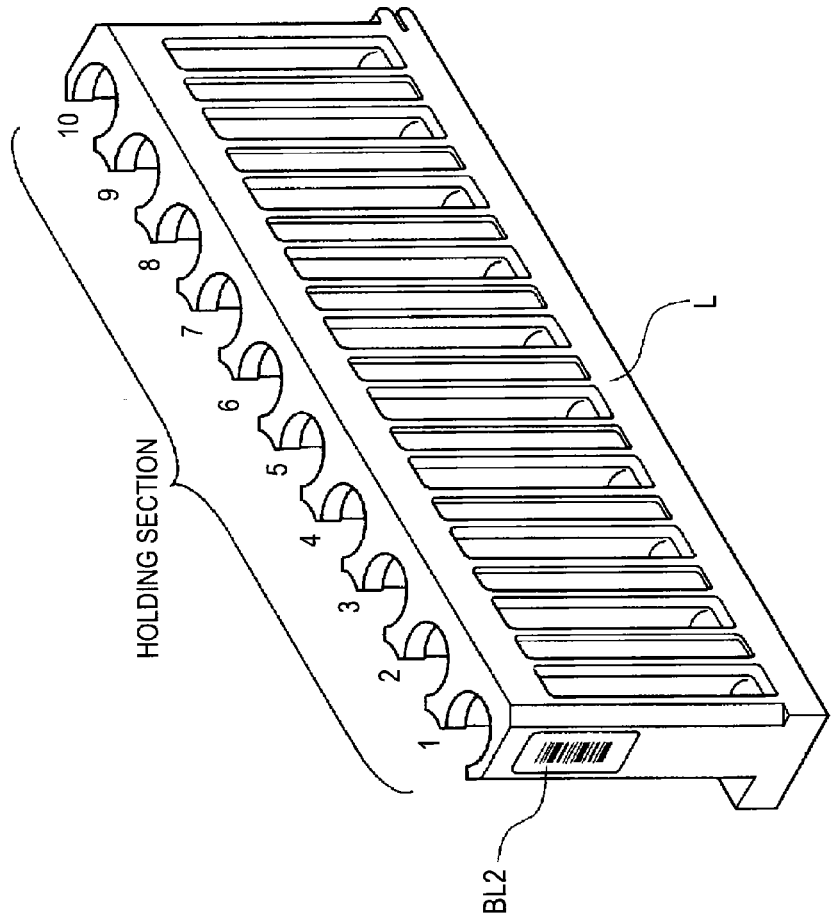

FIGS. 2A and 2B are a perspective view showing the appearance of a sample container and a perspective view showing the appearance of a sample rack, respectively.

Referring to FIG. 2A, a sample container T is a tubular container made of translucent glass or synthetic resin and is open at the upper end thereof. A blood sample collected from a patient is stored in the sample container and the opening at the upper end is sealed with a cap section C. A bar-code label BL1 is adhered to the side surface of the sample container T. A bar-code indicating a sample ID is printed on the bar-code label BL1.

Referring to FIG. 2B, in a sample rack L, ten holding sections are formed so as to vertically (uprightly) hold ten sample containers T side by side. A bar-code label BL2 is adhered to the side surface of the sample rack L. A bar-code indicating a rack ID is printed on the bar-code label BL2.

Returning to FIG. 1, the sample delivery unit 21a sequentially delivers placed sample racks L to the bar-code reading unit 22. The bar-code reading unit 22 reads a rack ID from the bar-code of the bar-code label BL2 adhered to the sample rack L delivered from the sample delivery unit 21a. In addition, the bar-code reading unit 22 reads a sample ID from the bar-code of the bar-code label BL1 adhered to the sample container T stored in the sample rack L. Moreover, the bar-code reading unit 22 delivers the sample rack L in which the reading has been completed to the sample delivery unit 21b. The sample delivery unit 21b sequentially delivers the sample racks L delivered from the bar-code reading unit 22 to the sample transport apparatus 3.

As shown in the drawing, the three sample transport apparatuses 3 are disposed in front of three measuring units 41, respectively. The two neighboring sample transport apparatuses 3 are connected to each other. The right end of the right sample transport apparatus 3 is connected to the sample delivery unit 21a of the sample input apparatus 2 and the left end of the left sample transport apparatus 3 is connected to the sample transport apparatus 5. As shown in the drawing, a notch is formed at both front ends of each sample transport apparatus 3 so as to transfer a sample rack L.

These three sample transport apparatuses 3 divide the cases into cases in which sample measurement is carried out and cases in which sample measurement is not carried out in the corresponding measuring units 41, respectively, to transport sample racks L by two transport paths. That is, as shown in the drawing, when the measuring unit 41 carries out sample measurement, a sample rack L is transported along the rear dashed-line arrow, and when the measuring unit 41 does not carry out sample measurement, a sample rack L is transported along the front dashed-line arrow.

The transport controller 8 controls the sample transport apparatus 3 when transporting a sample rack L along the front dashed-line arrow. In addition, an information processing apparatus 42 controls the sample transport apparatus 3 when transporting a sample rack L along the rear dashed-line arrow.

The blood cell analysis apparatus 4 is an optical flow cytometry type multiple blood cell analysis apparatus and includes the three measuring units 41 and the information processing apparatus 42. Hereinafter, for the sake of convenience, the three measuring units 41 will be referred to as M1, M2 and M3 sequentially from the right.

M1, M2 and M3 measures the blood sample stored in a sample container T. That is, each of M1, M2 and M3 takes out the sample container T from the sample rack L at a predetermined position on the transport path of the sample transport apparatus 3 disposed in front of the measuring unit. The blood sample stored in the sample container T is measured in M1, M2 and M3. When the measurement in M1, M2 and M3 is completed, the sample container T returns to the original holding section of the sample rack L.

The sample racks L which are sequentially delivered from the sample delivery unit 21*b* of the sample input apparatus 2 are alternately transported to M1 and M2. In this manner, two sample racks L can be measured in parallel by M1 and M2 and the entire measurement process is improved.

M3 is a measuring unit which is used in the re-examination. Whether re-measurement of M3 is required or not is determined in accordance with the measurement result of M1 or M2. When it is determined that re-examination is required by M1 or M2, the sample rack L storing a re-examination target sample is transported so as to perform the re-examination by M3. In this embodiment, such a determination is performed by the transport controller 8.

The information processing apparatus 42 is connected so as to communicate with the three measuring units 41 (M1, M2 and M3) and the transport controller 8. The information processing apparatus 42 controls the operations of the three measuring units 41 (M1, M2 and M3). In addition, the information processing apparatus 42 displays the analysis result based on the result of the measurement performed by the three measuring units 41 (M1, M2 and M3) on a display section 480. As the information processing apparatus 42, for example, a separate personal computer or a computer incorporated in the system can be used.

The sample transport apparatus 5 is disposed in front of the smear preparation apparatus 6 and includes a conveyor 51 and a rack slider 52. The transport apparatus 5 includes a control section 51*c* to control the operations of the conveyor 51 and the rack slider 52 in accordance with the command from the transport controller 8.

The conveyor 51 is provided with two rack transport passages 51*a* and 51*b* extending in a horizontal direction. The rack transport passage 51*a* near the smear preparation apparatus 6 is a measurement line for transporting a sample rack L which stores a sample to be used to prepare a smear by the smear preparation apparatus 6. On the other hand, the rack transport passage 51*b* away from the smear preparation apparatus 6 is a skip line for transporting a sample rack L which does not store a sample to be used to prepare a smear by the smear preparation apparatus 6.

The rack slider 52 is disposed at the right end of the conveyor 51 and is configured so as to be movable in a front-back direction. Due to the movement of the rack slider 52 in the front-back direction, a sample rack L which is delivered from the sample transport apparatus 3 disposed in front of M3 is delivered to the rack transport passage 51*a* or 51*b* by the rack slider 52.

The sample rack L passing through the sample transport apparatus 3 in front of M3 is stored in the rack slider 52. When distributing the sample rack L to the rack transport passage 51*a*, the rack slider 52 moves backward while storing the sample rack L and is positioned at the right side of the rack transport passage 51*a*. Then, the rack slider 52 pushes the sample rack L to the rack transport passage 51*a*. In this manner, the sample rack L is delivered to the rack transport passage 51*a*. On the other hand, when the sample rack L is distributed to the rack transport passage 51*b*, the rack slider 52 does not move backward and pushes the sample rack L to the rack transport passage 51*b*.

In the smear preparation apparatus 6, a smear of a blood sample is prepared. That is, first, the smear preparation apparatus 6 suctions a blood sample stored in a sample container T at a predetermined position on the rack transport passage 51*a*. Continuously, the suctioned blood sample is dropped onto a glass slide, thinly extended on the glass slide and then is dried. After that, a liquid dye is supplied to the glass slide to dye the blood on the glass slide and a smear is prepared.

Whether the preparation of a smear is required or not is determined in accordance with the measurement result of the three measuring units 41 (M1, M2 and M3). When it is determined that the preparation of a smear is required by the three measuring units 41 (M1, M2 and M3), the sample rack L storing a target sample is transported to the rack transport passage 51*a* so as to prepare a smear in the smear preparation apparatus 6. In this embodiment, such a determination is performed by the transport controller 8.

The sample storage apparatus 7 is configured such that a plurality of sample racks L are placed therein. The sample storage apparatus 7 receives and stores a sample rack L, in which the analysis or the preparation of a smear has been completed, from the rack transport passage 51*a* or 51*b* of the conveyor 51. The sample storage apparatus 7 may be configured such that sample racks L passing through the rack transport passage 51*a* and sample racks L passing through the rack transport 51*b* are distinguished and stored. In this manner, a user can easily distinguish the sample racks L from which the smear has been prepared from the sample racks L from which the smear has not been prepared.

The transport controller 8 controls the driving of the three sample transport apparatuses 3 and the sample transport apparatus 5, and monitors and controls the smear preparation apparatus 6. In addition, in order to properly transport a sample rack L, the transport controller 8 is connected to the sample input apparatus 2, the information processing apparatus 42 and the sample storage apparatus 7 so as to communicate therewith. As the transport controller 8, for example, a separate personal computer or a computer incorporated in the system can be used.

FIG. 3 is a top view showing the configuration of the sample transport apparatus 3, when viewed from the upper side. The sample transport apparatus 3 includes a pre-analysis rack holding section 310, a rack transport section 320, a post-analysis rack holding section 330 and a rack transport section 340.

In the case where the measurement is performed on a sample rack L, the sample rack L is sent to the lower-right position shown by the broken line in FIG. 3. After that, a rack pushing mechanism 342 moves backward and pushes the sample rack L to the front end of the pre-analysis rack holding section 310. When this state is detected by optical sensors 312*a* and 312*b* composed of a light-emitting section and a light-receiving section, rack feeding mechanisms 313*a* and 313*b* move backward while engaging with the front ends of the sample rack L, and the sample rack L is sent backward. In this manner, when the sample rack L is sent up to the right end position of the rack transport section 320, a switch 321 is turned on. In response to this, belts 322*a* and 322*b* are driven and the sample rack L is sent in the left direction. The rack feeding mechanisms 313*a* and 313*b* return to the transport position of a next sample rack L.

Then, the sample rack L arrives at the position of a sample container sensor 323. The sample container sensor 323 is a contact-type sensor. When a detection target sample container T, which is held in the sample rack L, passes through the position under the sample container sensor 323, the contact piece of the sample container sensor 323 is bent by the sample container T and thus the existence of the sample container T is detected.

At a position (hereinafter, referred to as "the sample supply position") positioned on the left side of the position, at which the sample container T has been detected by the sample container sensor 323, by a distance corresponding to one sample container, a hand section of the measuring unit 41 grips the sample container T and takes out the sample container T from the sample rack L. The removed sample container T returns to the sample rack L after used in the measurement in the measuring unit 41. The transport of the sample rack L stands by until the sample container T returns to the sample rack L.

In this manner, when the measurement of the samples in all of the sample containers T held in the sample rack L is completed, the sample rack L is sent up to the left end position of the rack transport section 320 shown by the broken line in FIG. 3 by the belts 322*a* and 322*b*. This state is detected by optical sensors 324*a* and 324*b* composed of a light-emitting section and a light-receiving section, and the driving of the belts 322*a* and 322*b* is stopped. After that, the sample rack L is sent to the rear end of the post-analysis rack holding section 330 by a rack pushing mechanism 325.

Then, rack feeding mechanisms 332*a* and 332*b* move forward while engaging with the rear ends of the sample rack L, and the sample rack L is sent forward. In this manner, the sample rack L is sent up to the left end position of the rack transport section 340.

In the case where the measurement is not performed on the sample rack L, the sample rack L is directly sent to the left end from the right end of the rack transport section 340 by a belt 341.

By controlling the transport of the sample rack L as described above, in the sample transport apparatus 3, a measurement line L1 as a transport line of the sample racks L routed through the sample supply position, and a skip line L2 as a transport line for directly carrying the sample racks L, carried from the right side without routed through the sample supply position, to the left apparatus are formed.

Sensors 314*a* and 314*b* are optical sensors composed of a light-emitting section and a light-receiving section, and detects whether or not the sample rack L exists at the right end positions of the rack transport passage 340 and the rack transport section 320 and on a transport passage 311 of the pre-analysis rack holding section 310. Sensors 333*a* and 333*b* are optical sensors composed of a light-emitting section and a light-receiving section, and detects whether or not the sample rack L exists at the left end positions of the rack transport passage 340 and the rack transport section 320 and on a transport passage 331 of the post-analysis rack holding section 330.

Figure 4:
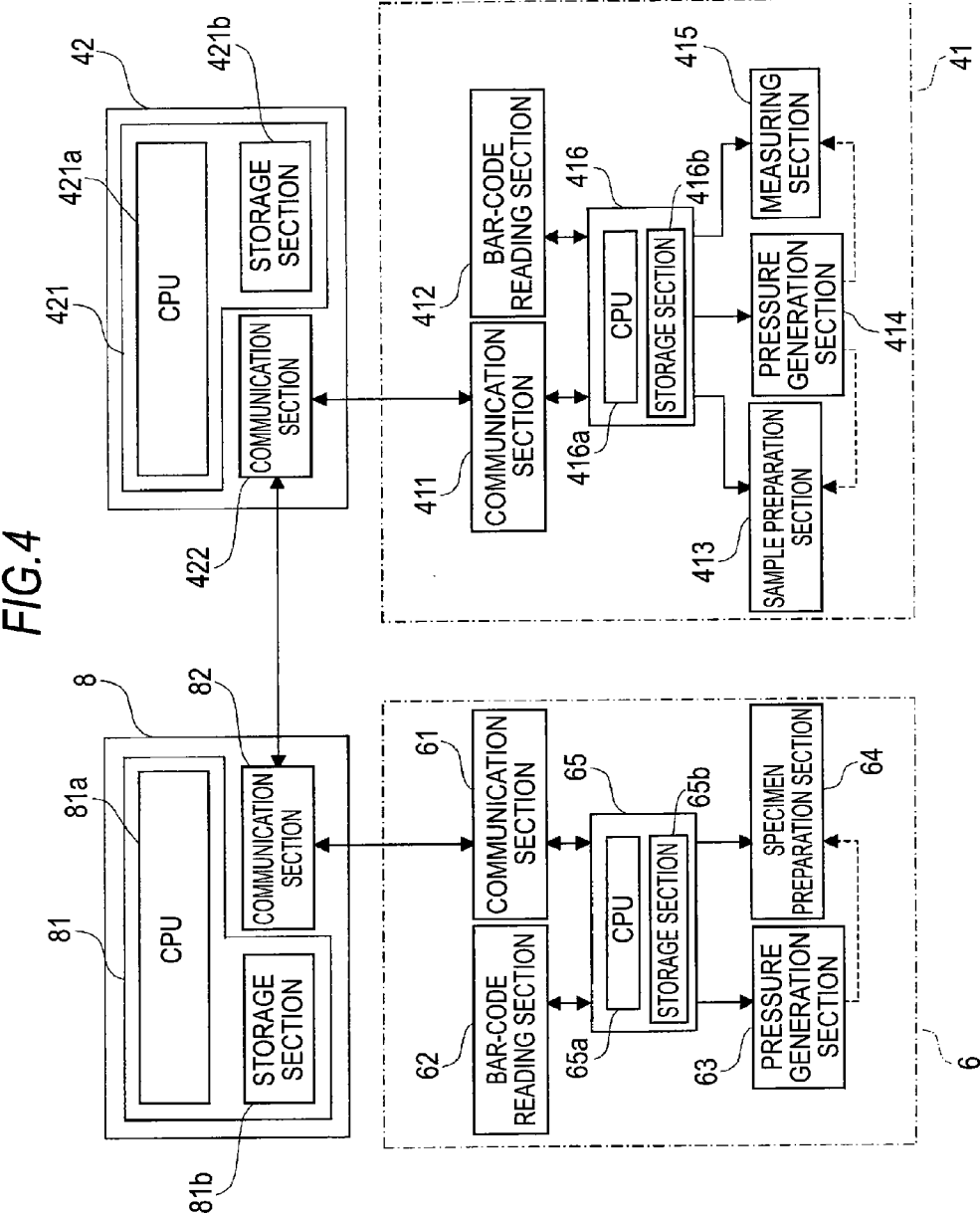
FIG. 4 is a diagram showing the configurations of a measuring unit, an information processing apparatus, a smear preparation apparatus and a transport controller.

FIG. 4 is a diagram showing the configurations of the measuring units 41 (M1, M2 and M3), the information processing apparatus 42, the smear preparation apparatus 6 and the transport controller 8. In FIG. 4, for the sake of convenience, only one measuring unit 41 is shown. However, other measuring units 41 also have the same configuration.

The measuring unit 41 includes a communication section 411, a bar-code reading section 412, a sample preparation section 413, a pressure generation section 414, a measuring section 415 and a control section 416.

The communication section 411 communicates with a communication section 422 of the information processing apparatus 42. The bar-code reading section 412 reads the bar-code label BL1 of a sample container T taken out into the measuring unit 41.

The sample preparation section 413 generates a measurement sample by suctioning and discharging the sample (blood) from a sample container T. The pressure generation section 414 includes a pneumatic pressure source to supply the pressure for fluid feeding to the sample preparation section 413 and the measuring section 415. The measuring section 415 includes a detector such as a flow cytometer, which is used in the blood cell analysis, to generate particle data by processing a detected signal. The control section 416 includes a CPU 416*a* and a storage section 416*b*. The storage section 416*b* includes storage means such as a ROM and a RAM. The storage section 416*b* stores the particle data obtained by the measuring section 415, the bar-code data read by the bar-code reading section 412 and the like. In addition, the storage section 416*b* is also used as a work area for the CPU 416*a*. The CPU 416*a* controls the sections in accordance with a control program stored in the ROM of the storage section 416*b*.

The information processing apparatus 42 includes a control section 421 and a communication section 422. The information processing apparatus 42 also includes an interface for performing a video output operation, an interface for performing an input operation from a keyboard or the like and a reading device such as a CD drive or a DVD drive. However, the descriptions thereof will be omitted.

The control section 421 includes a CPU 421*a* and a storage section 421*b*. The CPU 421*a* executes computer programs stored in the storage section 421*b*. The storage section 421*b* includes storage means such as a ROM, a RAM and a hard disk. The communication section 422 performs data communication between the three measuring units 41 and the transport controller 8.

The CPU 421*a* performs a blood analysis operation on the basis of the measurement result (particle data) received by the measuring unit 41 and displays the analysis result on the display section 480 (see FIG. 1). In addition, the CPU 421*a* transmits the analysis result to the transport controller 8. Moreover, as described above, the CPU 421*a* controls the transport of sample racks L on the basis of the detection signals of the various sensors and switches disposed in the sample transport apparatus 3. The CPU 421*a* also controls the operations of M1, M2 and M3 on the basis of the control command received from the transport controller 8. Such control operation will be described with reference to FIG. 7.

The smear preparation apparatus 6 includes a communication section 61, a bar-code reading section 62, a pressure generation section 63, a specimen preparation section 64 and a control section 65.

The communication section 61 communicates with a communication section 82 of the transport controller 8. The bar-code reading section 62 reads the bar-code label BL1 of a sample container T transported to the sample suction position of the smear preparation apparatus 6.

The pressure generation section 63 includes a pneumatic pressure source to supply the pressure for fluid feeding to the specimen preparation section 64. The specimen preparation section 64 prepares a smear by suctioning and discharging the sample (blood) from a sample container T transported to the sample suction position. The control section 65 includes a CPU 65*a* and a storage section 65*b*. The storage section 65*b* includes storage means such as a ROM and a RAM. The storage section 65*b* stores the bar-code data read by the bar-code reading section 62 and the like. In addition, the storage section 65*b* is also used as a work area for the CPU 65*a*. The CPU 65*a* controls the sections in accordance with a control program stored in the ROM of the storage section 65*b*.

The transport controller 8 includes a control section 81 and a communication section 82. The transport controller 8 also includes an interface for performing a video output operation, an interface for performing an input operation from a keyboard or the like and a reading device such as a CD drive or a DVD drive.

The control section 81 includes a CPU 81*a* and a storage section 81*b*. The CPU 81*a* executes computer programs stored in the storage section 81*b*. The storage section 81*b* includes storage means such as a ROM, a RAM and a hard disk. The communication section 82 performs data communication between the smear preparation apparatus 6 and the information processing apparatus 42.

The CPU 81a controls the driving of the three sample transport apparatuses 3 and the sample transport apparatus 5. In addition, the CPU 81a controls the operation of the smear preparation apparatus 6. Moreover, the CPU 81a determines whether the re-examination of M3 is required or not and whether the preparation of a smear is required or not on the basis of the sample analysis result received from the information processing apparatus 42, and controls the operations of M3 and the smear preparation apparatus 6 on the basis of the determination result. Such a control operation will be described with reference to FIGS. 5B and 6.

FIG. 5A is a diagram showing a processing flow of the transition to an inactive state of the measuring units 41 (M1, M2 and M3) according to this embodiment. The following process is monitored and controlled by the information processing apparatus 42.

In S1, by the control section 416 shown in FIG. 4, the operation situations of the measuring unit 41 and the sample transport apparatus 3 positioned in front of the measuring unit 41 are monitored.

In S2, in the monitoring of the operation situations, it is determined whether or not a predetermined period of time (15 minutes) has elapsed after a predetermined condition was met. When it is determined that a predetermined period of time (15 minutes) has elapsed (S2: YES), the process proceeds to S3. When it is determined that a predetermined period of time (15 minutes) has not elapsed (S2: NO), the process returns to S1 and the monitoring of the operation situations is continued.

Here, the predetermined condition is that a sample rack L (sample container T) is not detected by the sensors 312a and 312b, the sensors 314a and 314b and the sample container sensor 323. Regarding such predetermined condition, a user can change the setting in accordance with the utilization form. For example, the predetermined condition may be that a sample rack L (sample container T) is not detected by one or more of the sensors 312a and 312b, the sensors 314a and 314b and the sample container sensor 323. In addition, a predetermined period of time is 15 minutes in this specification, but also can be changed in accordance with the utilization form. This change is carried out from the input section of the information processing apparatus 42.

In S3, a transition process is performed such that the measuring unit 41 enters an inactive state. Here, the inactive state is a state in which the supply of electric power to the pneumatic pressure source in the pressure generation section 414 shown in FIG. 4 is stopped. In greater detail, when the transition process to the inactive state is started, a solenoid valve on the flow path is closed such that a sample and the like are not mixed and then the supply of electric power to the pneumatic pressure source is stopped.

Also in the smear preparation apparatus 6, when a predetermined condition, such as the passing of a predetermined period of time without the creation of a smear, is met as in the above-described measuring unit 41, a transition process is performed so as to achieve an inactive state. When the smear preparation apparatus 6 is shifted to an inactive state, the supply of electric power to the pneumatic pressure source (FIG. 4: pressure generation section 63) is stopped as in the measuring unit 41.

Next, processes of the transport controller 8 and the information processing apparatus 42 will be described with reference to the flowcharts shown in FIGS. 5B, 6, 7 and 8.

In this embodiment, when the re-examination of a sample is required, M3 is released from the inactive state, and when the preparation of a smear is required, the smear preparation apparatus 6 is released from the inactive state. The determination of whether the re-examination is required or not and whether and the preparation of a smear is required or not is performed by the transport controller 8.

FIG. 5B is a diagram showing a processing flow of the transport controller 8. A sample measurement process (FIGS. 6 and 7) is performed in parallel to this processing flow and the measurement result is supplied to the transport controller 8 as needed.

In S101, the transport controller 8 transports a sample rack L, which is delivered from the sample delivery unit 21b of the sample input apparatus 2, to the sample transport apparatus 3 in front of M1 or M2. Accordingly, the sample rack L is moved up to the position positioned anterior to the pre-analysis rack holding section 310 of the sample transport apparatus 3 in front of M1 or M2. Continuously, the transport controller 8 drives the rack pushing mechanism 342 to push the sample rack L to the pre-analysis rack holding section 310.

The sample rack L pushed to the pre-analysis rack holding section 310 is transported along the measurement line L1 as described above and thus positioned at the sample supply position. After that, the measurement is performed by M1 or M2.

In S102, the transport controller 8 determines whether the re-examination of M3 is required or not and whether the preparation of a smear in the smear preparation apparatus 6 is required or not on the basis of the measurement result of M1 or M2. Such a determination is sequentially performed on all the sample containers T held in the sample rack L.

Figure 6:
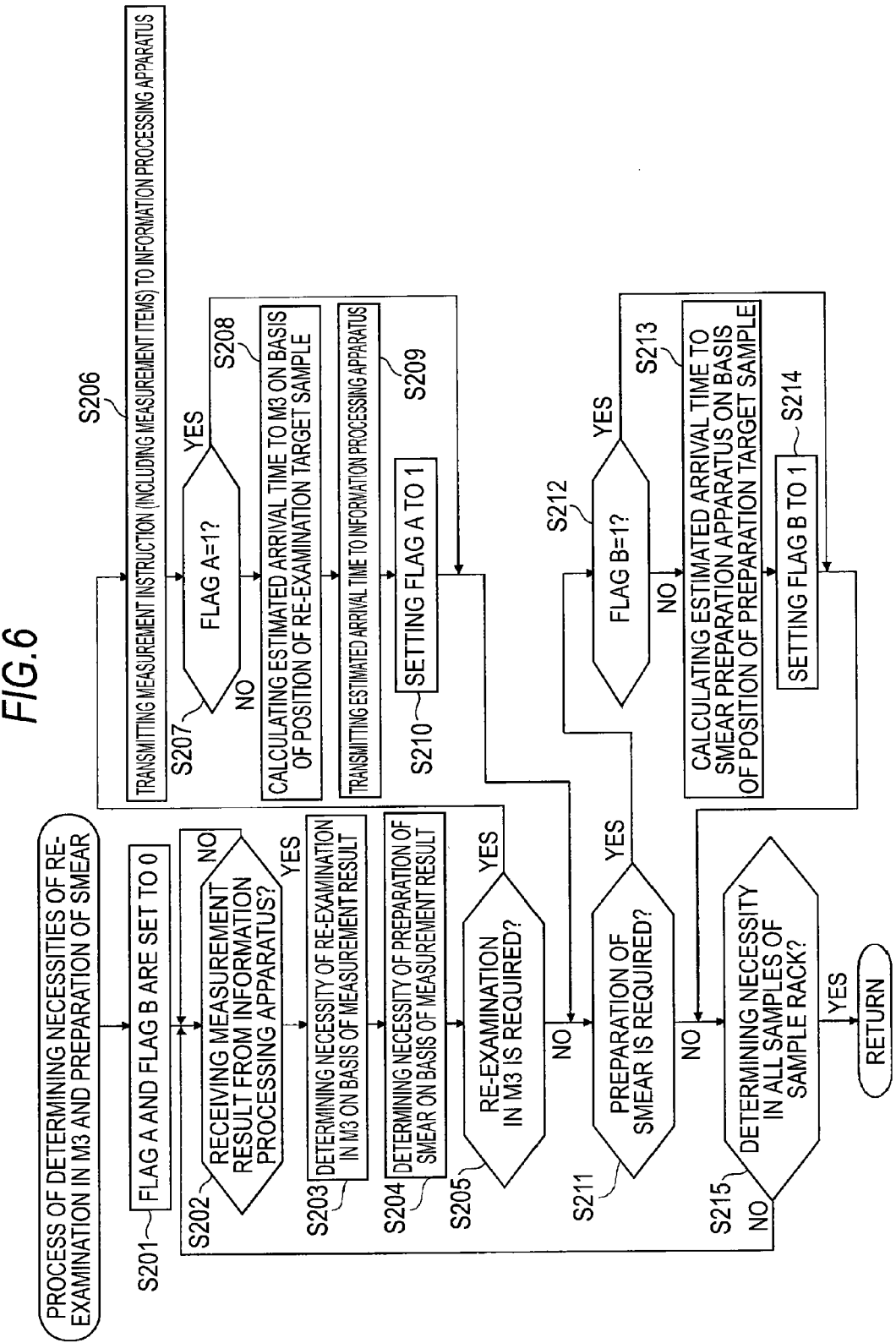
FIG. 6 is a flowchart showing the content of the process of S102 of FIG. 5B.

FIG. 6 is a flowchart showing the detailed processing content of S102.

In S201, a flag A and a flag B are set to 0, respectively.

In S202, it is determined whether or not the result of the measurement performed in M1 or M2 has been supplied from the information processing apparatus 42. Here, in addition to the bar-code data read from a measurement target sample container T, the measurement result is transmitted to the transport controller 8.

When the measurement result relating to a predetermined sample container T is received from the information processing apparatus 42 (S202: YES), the transport controller 8 determines whether or not it is required to perform the re-examination on the sample of the sample container T by M3 (S203) and whether or not it is required to perform the preparation of a smear in the smear preparation apparatus 6 (S204) on the basis of the measurement result. Whether the re-examination is required or not and whether the preparation of a smear is required or not are determined by comparing the measurement result of the sample with a predetermined threshold based on the age, sex and the like of a sample provider (patient). The age, sex and the like of the sample provider (patient) are obtained from a host computer on the basis of the bar-code data of the sample container T.

When the re-examination and the preparation of a smear are not required as a result of the determination of S203 and S204 (S205: NO, S211: NO), the transport controller 8 determines whether or not the determination of the necessity of the re-examination and smear preparation has been performed on the samples in all the sample containers T held in the sample rack L (S215). In this determination, when a sample container T which is not subjected to the necessity determination remains (S215: NO), the transport controller 8 return to S202 and waits for the transmission of the measurement result relating to a next sample container T.

In the determination of S215, the transport controller 8 inquires of the information processing apparatus 42 whether or not the measurement has been completed in all the sample containers T held in the sample rack L. Regarding this inquiry, when a response of the end of the measurement is gotten from the information processing apparatus 42, the transport controller 8 determines the result is YES in S215.

When the determination result in S203 is "the re-examination is required" (S205: YES), the transport controller 8 transmits a measurement instruction indicating that the re-examination in M3 is required, measurement items of the re-examination and bar-code information for specifying a re-examination target sample container T to the information processing apparatus 42. Continuously, the transport controller 8 determines whether a value of the flag A is set to 1 or not (S207). When the value of the flag A is 1 (S207: YES), the process proceeds to S211, and when the value of the flag A is not 1 (S207: NO), the process proceeds to S208. When the value of the flag A is 1, a transmitting process of the estimated arrival time in S209 is already completed and thus the processes of S208 and S209 are skipped.

In S208, depending on the holding position of the sample container T storing the sample which becomes a re-examination target in the sample rack L, the estimated time of arrival to M3 of the sample rack L holding the sample container T under measurement is calculated.

For example, such a calculation of the estimated arrival time is performed as follows.

As shown in FIGS. 2A and 2B, ten holding sections are formed in the sample rack L. Accordingly, when the sample containers T held in the sample rack L are sequentially subjected to the measurement from the end, the time required for the sample rack L to reach M3 is changed depending on the holding section of the sample container T (hereinafter, this sample container will be particularly referred to as "the sample container Tf") storing the sample which is initially required to be re-examined among the sample containers T.

For example, when the sample container Tf is held in a holding section (holding position 1) closest to M3, the sample rack L is not transported toward M3 until all the samples in the sample containers T stored in the remaining holding sections are measured. In this case, the time required from when it is determined that the sample container Tf is required to be re-examined until the sample rack L arrives at M3 is increased. On the other hand, when the sample container Tf is held in a holding section (holding position 10) most distant from M3, there are no remaining sample containers T to be measured in the sample rack L and thus the sample rack L is directly transported toward M3. Accordingly, the time required from when it is determined that the sample container Tf is required to be re-examined until the sample rack L arrives at M3 is decreased.

In addition, the time required for the sample rack L to reach M3 is also changed depending on the number of other sample racks L which are present on the transport path to M3. That is, when many other sample racks L are present on such transport path, these sample racks L block the transport path and thus the transport of the sample rack L holding the sample container Tf is disrupted. In this case, the period of time from when the sample rack L is transported toward M3 until the sample rack L arrives at M3 is increased.

The time required until the sample rack L arrives at M3 is also changed depending on from which one of M1 and M2 the sample rack L is transported. That is, since M1 is more distant from M3 than M2, the period of time from when the sample rack L is transported from M1 until the sample rack L arrives at M3 is longer than the period of time from when the sample rack L is transported from M2 until the sample rack L arrives at M3.

In S208, in consideration of these change factors, the amount of time required for the sample rack L holding the sample container Tf to reach M3 is obtained by the transport controller 8, and the estimated arrival time is calculated from this amount of time and the required time. The estimated arrival time is transmitted to the information processing apparatus 42 (S209). Continuously, the flag A is set to 1 (S210). In this manner, the transmission of the estimated time of arrival to M3 is stored.

On the basis of the measurement result received from the information processing apparatus 42, when it is determined that the preparation of a smear is required in S204 (S211: YES), the process proceeds to S212. When it is determined that the preparation of a smear is not required (S211: NO), the process proceeds to S215.

In S212, the transport controller 8 determines whether a value of the flag B is 1 or not. Here, when the value of the flag B is 1 (S212: YES), the process proceeds to S215, and when the value of the flag B is not 1 (S212: NO), the process proceeds to S213. When the value of the flag B is 1, the calculation of the estimated arrival time in S213 is already completed and thus the process of S213 is skipped.

In S213, depending on the holding position of the sample container T storing the sample which becomes a target of the preparation of a smear in the sample rack L, the estimated time of arrival of the sample rack L holding the sample container T under measurement to the smear preparation apparatus 6 is calculated as in the above-described S208. The estimated arrival time is held by the transport controller 8 and the flag B is set to 1 (S214). In this manner, the calculation and holding of the estimated time of arrival to the smear preparation apparatus 6 is stored.

In accordance with the above-described processes, when the necessity of the re-examination in M3 and the necessity of the preparation of a smear are determined (S215: YES) in all the samples of the sample rack L in which the measurement is performed, the necessity determination process (S102) of FIG. 5B is completed.

As described above, the calculation of the estimated arrival time in S208 and S213 is performed when the sample container T storing the sample in which it is initially determined that the re-examination is required or the preparation of a smear is required is generated among a plurality of the sample containers T stored in the sample rack L.

Returning to FIG. 5B, in accordance with the above-described processes, when the determination process of the necessity of the re-examination in M3 and the necessity of the preparation of a smear is completed in S102, the transport controller 8 refers to the state of the flag A (S103). Here, when a value of the flag A is 1 (S103: YES), the sample container T which is required to be re-examined is held in the sample rack L as a transport target, so the transport controller 8 transports the sample rack L, in which the measurement in M1 or M2 has been completed to the sample transport apparatus 3 in front of M3 (S104). In response to this, the sample rack L is transported along the measurement line L1, the sample which is required to be re-examined is measured by M3 and the measurement result is transmitted to the transport controller from the information processing apparatus 42 (FIG. 7: S313). When the value of the flag A is not 1 (S103: NO), the process proceeds to S106.

In S105, on the basis of the measurement result received from the information processing apparatus 42, the necessity of the preparation of a smear in the smear preparation apparatus 6 is determined. In S105, the process in which the processing steps of S201, S203, and S205 to S210 are omitted in FIG. 6 is performed.

Next, the transport controller 8 refers to the value of the flag B (S106). When the value of the flag B is 1 (S106: YES), the transport controller 8 transports the sample rack L in which the measurement of M1 to M3 has been completed to the smear preparation apparatus 6 to prepare a smear (S107). When the value of the flag B is not 1 (S106: NO), the process proceeds to S108. That is, when the value of the flag B is 1, the sample container T in which it is determined that the preparation of a smear is required is included in all the sample containers T held in the sample rack L as a transport target. In this case, the sample rack L is transported to the smear preparation apparatus 6 to prepare a smear of the target sample. The smear preparing process will be described with reference to FIG. 8B.

In S108, the transport controller 8 transports the sample rack L to the sample storage apparatus 7. So, the process relating to the sample rack L is completed.

FIG. 7 is a diagram showing a processing flow of the information processing apparatus 42.

By the control operation of the transport controller 8, the sample rack L is pushed to the pre-analysis rack holding section 310 of M1 or M2. The information processing apparatus 42 transports the sample rack L pushed to the pre-analysis rack holding section 310 to the sample supply position in M1 or M2 (S301) and the sample stored in a sample container T is measured (S302). M1 or M2 transmits the data detected from the sample container T to the information processing apparatus 42.

When receiving the detection data from M1 or M2 (S303: YES), the information processing apparatus 42 analyzes the detection data and obtains the measurement result (S304). Next, the information processing apparatus 42 transmits the obtained measurement result to the transport controller 8 and inquires of the transport controller 8 whether or not re-examination in M3 is required (S305). When the re-examination in M3 is required, a re-examination instruction and measurement items of the re-examination are transmitted from the transport controller 8 in S206 of FIG. 6.

After that, the information processing apparatus 42 determines whether the measurement of all the sample containers T held in the sample rack L has been completed or not in M1 or M2 (S306). When the measurement of all the sample containers T held in the sample rack L has been completed (S306: YES), the process proceeds to S307. When the measurement of all the sample containers T held in the sample rack L has not been completed (S306: NO), the process returns to S301 and the steps S301 to S305 are repeatedly performed until the measurement of all the sample containers T held in the sample rack L is completed.

The information processing apparatus 42 determines whether or not a sample in which it is determined that the re-examination in M3 is required is included in the sample rack L on the basis of the response to the inquiry in S305 (S307). When the re-examination is required, the sample rack L is transported to the pre-analysis rack holding section 310 of M3 in S104 of FIG. 5B. The information processing apparatus 42 issues a command to the sample transport apparatus 3 such that the sample rack L which is pushed to the pre-analysis rack holding section 310 as described above is transported toward the sample supply position (S308). When the re-examination in M3 is not required (S307: NO), the process of the information processing apparatus 42 with respect to the sample rack L is completed.

In response to S308, when the sample container T storing the sample in which it is determined that the re-examination is required is positioned at the sample supply position of M3, the information processing apparatus 42 determines whether M3 is in an inactive state or not (S309). If M3 is in an inactive state when it is determined that the re-examination is required in S102 of FIG. 5B, M3 is subjected to a process of releasing the inactive state. The inactive state releasing process will be described with reference to FIG. 8A. The information processing apparatus 42 advances a process of S310 when M3 is not in an inactive state (S309: NO), and waits for the completion of the release of the inactive state of M3 when M3 is in an inactive state (S309: YES). In this embodiment, since the release of the inactive state is started at an appropriate timing, M3 is in an active state when the sample container is transported to the sample supply position of M3. Accordingly, the step S309 for waiting for the completion of the release of the inactive state of M3 can be omitted. However, by executing this step, taking the sample in M3 in an inactive state can be prevented when the release of the inactive state takes more time than an assumed time.

In S310, the information processing apparatus 42 issues an instruction so as to advance the measurement of the sample in which it is determined that the re-examination is required. In response to this, when receiving detection data from M3 (S311: YES), the information processing apparatus 42 analyzes the detection data in terms of the designated measurement items and obtains the measurement result (S312). Then, the information processing apparatus 42 transmits the obtained measurement result to the transport controller 8 (S313). The transmitted measurement result is used in the determination of the necessity of the preparation of a smear in S105 of FIG. 5B.

Then, the information processing apparatus 42 determines whether the measurement has been completed in all the sample containers T which are held in the sample rack L and required to be re-examined (S314). When the measurement has been completed in these all sample containers T (S314: YES), the process of the information processing apparatus 42 with respect to the sample rack L is completed. When the measurement of all the sample containers T which are required to be re-examined has not been completed (S314: NO), the process returns to S308. In this case, the steps S308 to S313 are repeatedly performed until the measurement of all the sample containers T which are required to be re-examined is completed.

FIG. 8A is a flowchart of the process for releasing the inactive state of M3.

When the transport controller 8 determines that the re-examination in M3 is required, in S208 of FIG. 6, the estimated time of arrival of the sample rack L under measurement to M3 is calculated and transmitted to the information processing apparatus 42. When receiving the estimated arrival time (S401: YES), the information processing apparatus 42 determines whether M3 is in an inactive state or not (S402). When M3 is not in an inactive state (S402: NO), the information processing apparatus 42 transmits an instruction for prohibiting the transition to the inactive state to M3 (S403) and the processing flow is completed. When M3 is in an inactive state (S402: YES), it is determined whether or not the present time has reached a predetermined time earlier than the estimated arrival time (S404). The step S403 for prohibiting shifting of M3 to the inactive state can be omitted. However, by executing this step, the need for starting the release of an inactive state being generated soon after M3 enters the inactive state can be prevented. Accordingly, it is possible to cut power consumption caused by frequent repetition of the transition to an inactive state and the release.

The information processing apparatus 42, when it is determined that the present time has reached a predetermined time earlier than the estimated arrival time (S404: YES), M3 is instructed to start the release of the inactive state (S405) and the process is completed. The predetermined time in S404 is set on the basis of the period of time from when M3 starts the release of the inactive state until the release is completed.

FIG. 8B is a flowchart showing the content of the smear preparing process in S107 of FIG. 5B. Such a process is performed by the transport controller 8.

On the basis of S102 or S105 of FIG. 5B, when the sample rack L includes a sample in which it is determined that the preparation of a smear is required, the transport controller 8 transports the sample container T storing the sample in which it is determined that the preparation of a smear is required to the sample suction position of the smear preparation apparatus 6 (S221).

When the sample container T storing the sample in which it is determined that the preparation of a smear is required is positioned at the sample suction position of the smear preparation apparatus 6, the transport controller 8 determines whether the smear preparation apparatus 6 is in an inactive state or not (S222).

In the case where the smear preparation apparatus 6 is in an inactive state when it is determined that the preparation of a smear is required in S102 or S105 of FIG. 5B, a process of releasing the inactive state of the smear preparation apparatus 6 is performed. Such inactive state releasing process is performed by the same process as in FIG. 8A. That is, the transport controller 8 determines whether the smear preparation apparatus 6 is in an inactive state or not, and prohibits shifting of the smear preparation apparatus 6 to the inactive state when the smear preparation apparatus is not in the inactive state. When the smear preparation apparatus 6 is in the inactive state, the transport controller determines whether or not the present time has reached a predetermined time earlier than the estimated arrival time calculated in S102 or S105 of FIG. 5B. When the present time has reached a predetermined time earlier than the estimated arrival time, the transport controller 8 releases the inactive state of the smear preparation apparatus 6.

When the smear preparation apparatus 6 is not in the inactive state (S222: NO), the process proceeds to S223, and when the smear preparation apparatus is in the inactive state (S222: YES), the process stands by until the release of the inactive state is completed. The step S222 can be omitted as in the case of the above-described step S309. However, by executing this step, taking the sample into the smear preparation apparatus 6 is prevented in an inactive state when the release of the inactive state takes more time than an assumed time.

In S223, the transport controller 8 causes the smear preparation apparatus 6 to prepare a smear of the sample in which it is determined that the preparation of a smear is required. In addition, the transport controller 8 determines whether or not the process has been completed in all the sample containers T in which it is determined that the preparation of a smear is required (S224). When the process has been completed in these all sample containers T (S224: YES), the preparation of a smear is completed. When the process has not been completed in all the sample containers T in which it is determined that the preparation of a smear is required (S224: NO), the process returns to S221. In this case, the steps S221 to S224 are repeatedly performed until the preparation of a smear is completed in all the sample containers T which are held in the sample rack L and in which it is determined that the preparation of a smear is required.

According to this embodiment, when M3 and the smear preparation apparatus 6 are not used for a predetermined time, M3 and the smear preparation apparatus 6 are shifted to an inactive state. Accordingly, it is possible to cut power consumption in M3 and the smear preparation apparatus 6. In addition, when the re-examination in M3 is required by the measurement result of M1 or M2, the inactive state of M3 is released, and when the preparation of a smear is required by the measurement result of M1 to M3, the inactive state of the smear preparation apparatus 6 is released. Accordingly, even when M3 and the smear preparation apparatus 6 are in an inactive state, the re-examination in M3 and the preparation of a smear in the smear preparation apparatus 6 can be performed without delay.

In addition, according to this embodiment, when it is determined that the re-examination or the preparation of a smear is required, the estimated time of arrival of the sample rack L to M3 or the smear preparation apparatus 6 is calculated, and on the basis of the estimated time, the inactive state of M3 and the smear preparation apparatus 6 is released. Accordingly, power consumption of M3 and the smear preparation apparatus 6 can be more effectively cut and the re-examination or the preparation of a smear can be smoothly performed.

2. Second Embodiment

In the first embodiment, the transport controller 8 determines the necessity of the re-examination and the necessity of the preparation of a smear. However in this embodiment, the information processing apparatus 42 determines these necessities.

Figure 9:
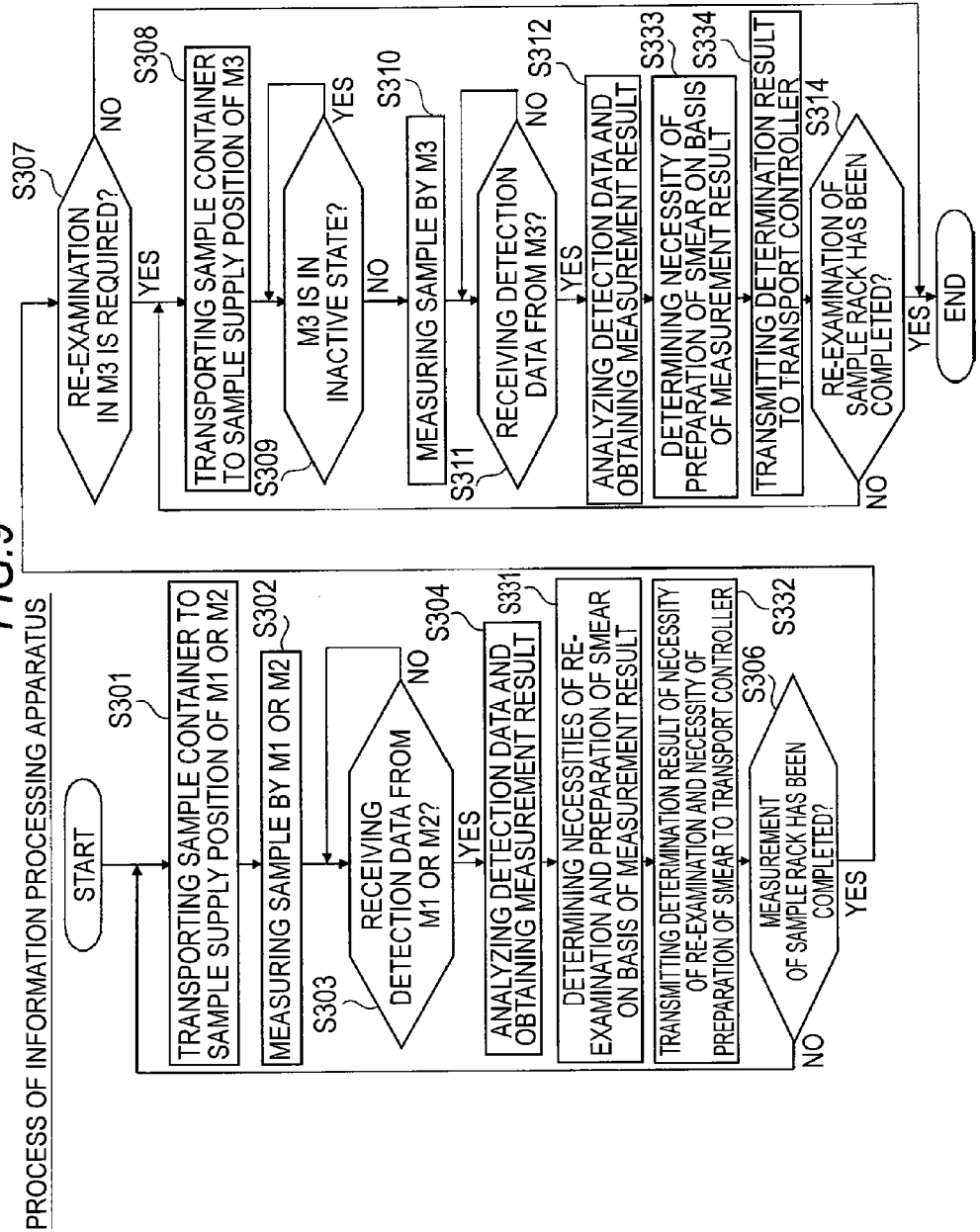
FIG. 9 is a flowchart showing a process of an information processing apparatus according to a second embodiment.

FIG. 9 is a flowchart showing a process of the information processing apparatus 42. The steps S305 and S313 (see FIG. 7) shown in the first embodiment are replaced with steps S331 and S333, respectively, in this embodiment. In addition, steps S332 and S334 are added. The processing flow is the same as in the above-described first embodiment, except for them.

In S331, on the basis of the measurement result of M1 or M2, the information processing apparatus 42 determines the necessity of the re-examination in M3 and the necessity of the preparation of a smear in the smear preparation apparatus 6, and in S332, the information processing apparatus 42 transmits the determination result of the necessities of the re-examination and the preparation of a smear and the bar-code data of the corresponding sample container T to the transport controller 8. In addition, in S333, on the basis of the measurement result of M3, the information processing apparatus 42 determines the necessity of the preparation of a smear in the smear preparation apparatus 6, and in S334, the information processing apparatus transmits the determination result and the bar-code data of the corresponding sample container T to the transport controller 8.

In this first embodiment, the determination of S307 is carried out on the basis of the command received from the transport controller 8. However, in this embodiment, the determination of S307 is carried out on the basis of the result of the determination of the information processing apparatus 42 in S331.

Figure 10:
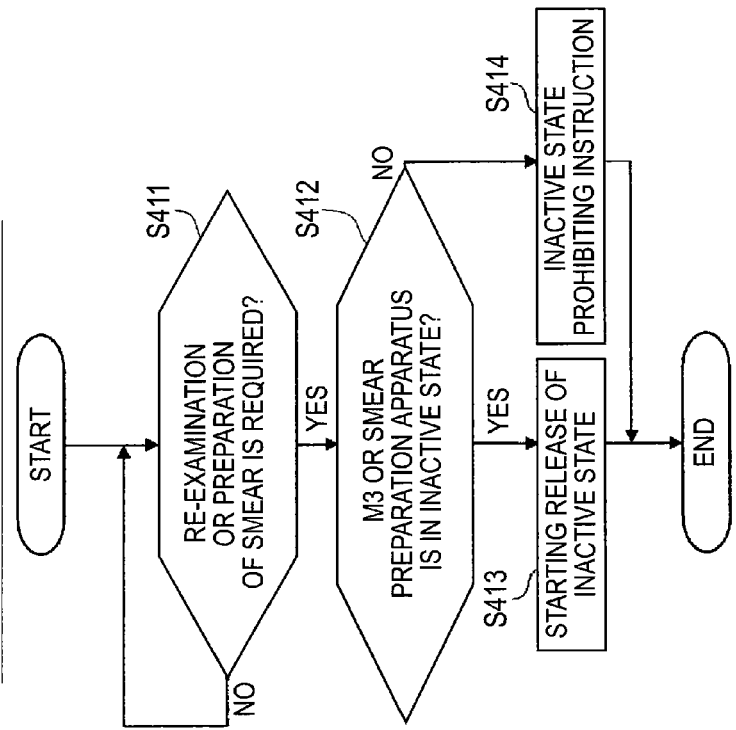
FIG. 10A is a flowchart showing a process of a transport controller according to the second embodiment.
FIG. 10B is a flowchart showing an inactive state releasing process according to the second embodiment.

FIG. 10A is a flowchart showing a process of the transport controller 8 according to this embodiment. In this embodiment, the steps S102 and S105 shown in the first embodiment (see FIG. 5B) are omitted and the steps S103 and S106 are changed into steps S111 and S112, respectively. The processing flow is the same as in the above-described first embodiment, except for these changes.

In S111, the transport controller 8 determines whether the re-examination in M3 is required or not on the basis of the determination result transmitted from the information processing apparatus 42 in S332 of FIG. 9. In addition, in S112, the transport controller 8 determines whether the re-examination in M3 is required or not on the basis of the determination result transmitted from the information processing apparatus 42 in S332 or S334 of FIG. 9.

FIG. 10B is a flowchart of processing for releasing the inactive state of M3 or the smear preparation apparatus 6. The releasing process for M3 is performed by the information processing apparatus and the releasing process for the smear preparation apparatus 6 is performed by the transport controller 8.

In the inactive state releasing process shown in the first embodiment (see FIG. 8A), when the present time has reached a predetermined time earlier than the estimated arrival time of the sample rack L, the inactive state of M3 or the smear preparation apparatus 6 is released. However, in this embodiment, in response to the generation of a sample container Tf in which it is initially determined that the re-examination or the preparation of a smear is required among the sample containers T held in the sample rack L, the inactive state of M3 or the smear preparation apparatus 6 is released. That is, when the sample container Tf is generated (S411), it is determined whether M3 or the smear preparation apparatus 6 is in an inactive state or not (S412). When M3 or the smear preparation apparatus 6 is not in an inactive state (S412: NO), the transition to the inactive state is prohibited S414), and when M3 or the smear preparation apparatus 6 is in an inactive state (S412: YES), the inactive state is released (S413).

In this manner, when M3 or the smear preparation apparatus 6 is in an inactive state, the inactive state of M3 or the smear preparation apparatus 6 can be released as in the first embodiment.

Here, the inactive state is directly released in S413, but in place of this, the inactive state may be released after a certain period of time has elapsed from when it was determined that the re-examination or the preparation of a smear is required. In this case, regarding the certain period of time, a fixed period of time is set by assuming the arrival time of the sample rack L to M3 or the smear preparation apparatus 6. In addition, the certain period of time may be changed depending on whether the sample rack L is transported to M3 from M1 or M2, or whether the sample rack L is transported to the smear preparation apparatus 6 from M1, M2 or M3.

According to this embodiment, the information processing apparatus 42 determines the necessity of the re-examination in M3 and the necessity of the preparation of a smear in the smear preparation apparatus 6. Accordingly, the re-examination in M3 and the preparation of a smear in the smear preparation apparatus 6 can be performed without delay while cutting power consumption of M3 and the smear preparation apparatus 6.

3. Third Embodiment

A sample processing apparatus according to a third embodiment will be described with reference to the drawings.

Figure 11:
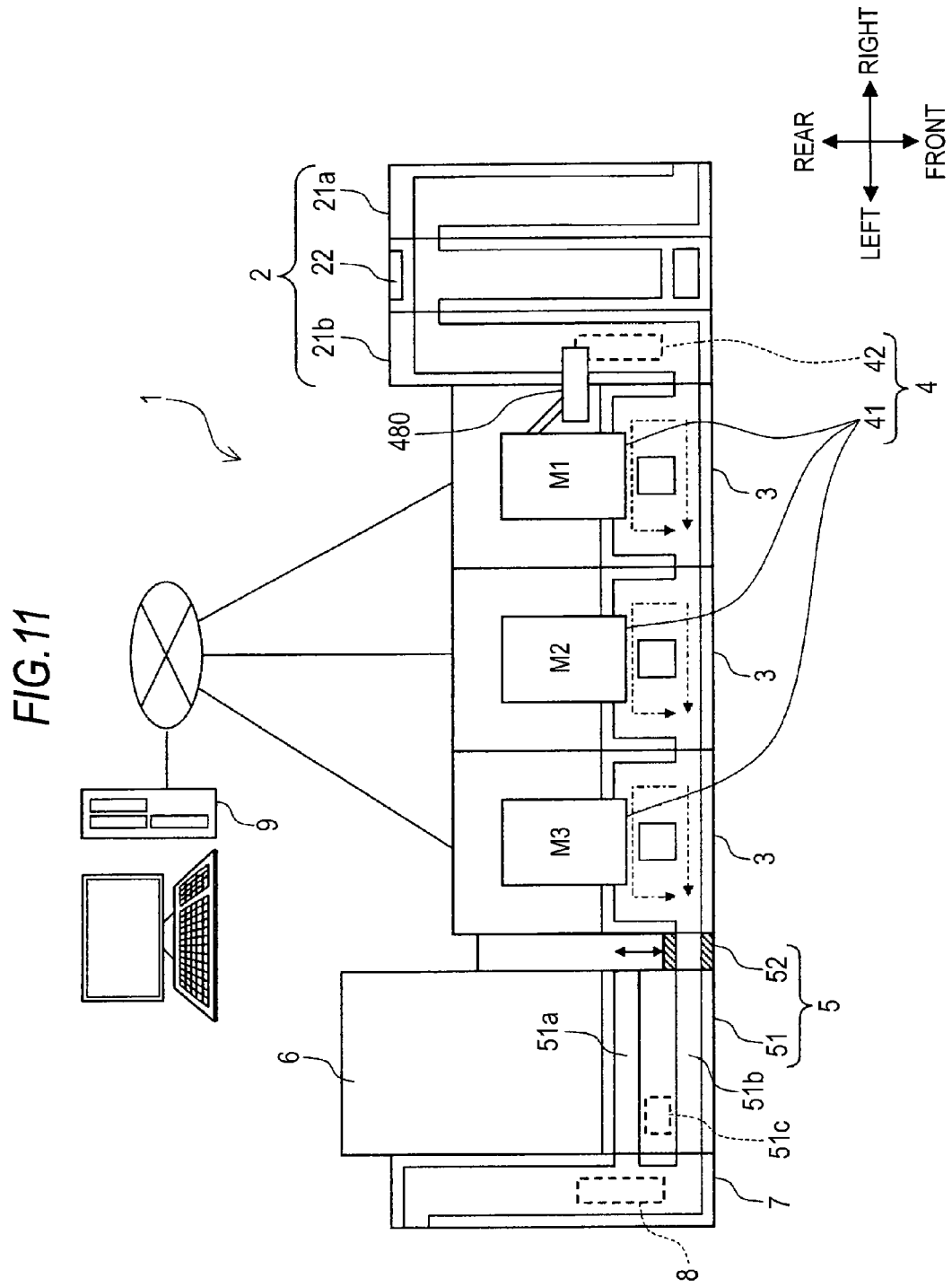
FIG. 11 is a diagram showing the configuration of a sample processing system according to a third embodiment.

FIG. 11 is a diagram showing a sample processing system 1. In this embodiment, a host computer 9 determines the necessity of the re-examination in M3 and the necessity of the preparation of a smear in the smear preparation apparatus 6.

The host computer 9 has the same configuration as in the information processing apparatus 42 shown in FIG. 4. The host computer 9 is connected to a communication network and can communicate with the information processing apparatus 42, sample input apparatus 2, sample transport apparatus 3, sample storage apparatus 7 and transport controller 8.

In addition, on the hard disk of the host computer 9, measurement orders are stored. When receiving request data of a measurement order including a sample ID from another apparatus, the host computer 9 reads measurement data corresponding to the sample ID from the hard disk and transmits the measurement data to the request source apparatus.

Figure 12:
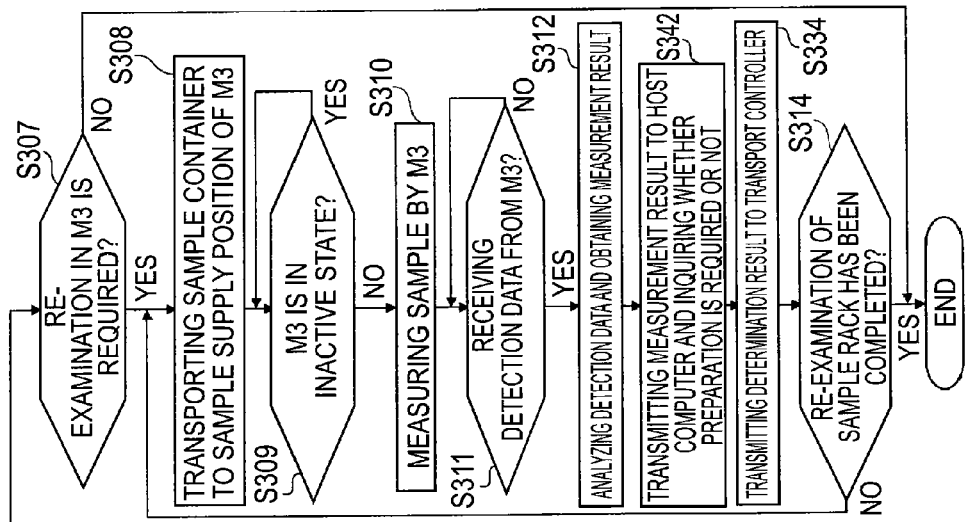
FIG. 12 is a flowchart showing a process of an information processing apparatus according to the third embodiment.

FIG. 12 is a diagram showing a processing flow of the information processing apparatus 42. The steps S331 and S333 (see FIG. 9) shown in the above-described second embodiment are replaced with steps S341 and S342, respectively, in this embodiment. The processing flow is the same as in the above-described first embodiment, except for this change.

In S341, the information processing apparatus 42 transmits the measurement result of M1 or M2 and inquires of the host computer whether or not the re-examination in M3 is required and whether or not the preparation of a smear in the smear preparation apparatus 6 is required. In response to this, when receiving the determination result from the host computer 9, the information processing apparatus 42 transmits the determination result of the necessity of the preparation of a smear to the transport controller 8 (S332). In addition, in S342, the information processing apparatus 42 transmits the measurement result of M3 to the host computer 9 and inquires of the host computer whether or not the preparation of a smear in the smear preparation apparatus 6 is required. In response to this, when receiving the determination result from the host computer 9, the information processing apparatus 42 transmits the determination result to the transport controller 8 (S334).

As described above, the embodiments of the present invention have been described, but the embodiments of the present invention are not limited thereto.

For example, in the above-described three embodiments, blood is exemplified as a measurement target. However, urine may be a measurement target. That is, the present invention also can be applied to sample processing apparatuses examining urine and can be further applied to clinical sample examining apparatuses examining other clinical samples.

In the above-described three embodiments, it can be initially determined that, for example, the sample in the third sample container T among ten sample containers T held in a sample rack L is required to be subjected to the "preparation of a smear only" and then it can be determined that the sample in the fifth sample container T is required to be subjected to a "re-examination". In this case, regarding the third sample container T, when estimated arrival time is calculated on the assumption that the sample rack L passes through the skip line L2 without passing through the measurement line L1 of M3 so as to be transported to the smear preparation apparatus 6, the sample rack L actually passes through the measurement line L1 of M3 and thus the calculated estimated arrival time is earlier than the estimated arrival time of the case where a re-examination is performed in M3. Accordingly, in this case, at a timing at which it is determined that the sample in the fifth sample container T is required to be re-examined, the sample rack L may pass through the measurement line L1 of M3 such that the estimated time of arrival to the smear preparation apparatus 6 is modified.

In the above-described second and third embodiments, the estimated arrival time of a sample rack L is not calculated. However, also in the above-described second and third embodiments, the measurement result of M1 to M3 may be transmitted from the information processing apparatus 42 to the transport controller 8 and the transport controller 8 may calculate the estimated arrival time of a sample rack L as in the above-described first embodiment. In addition, such a calculation of the estimated arrival time may be performed in the information processing apparatus 42.

Figure 13:
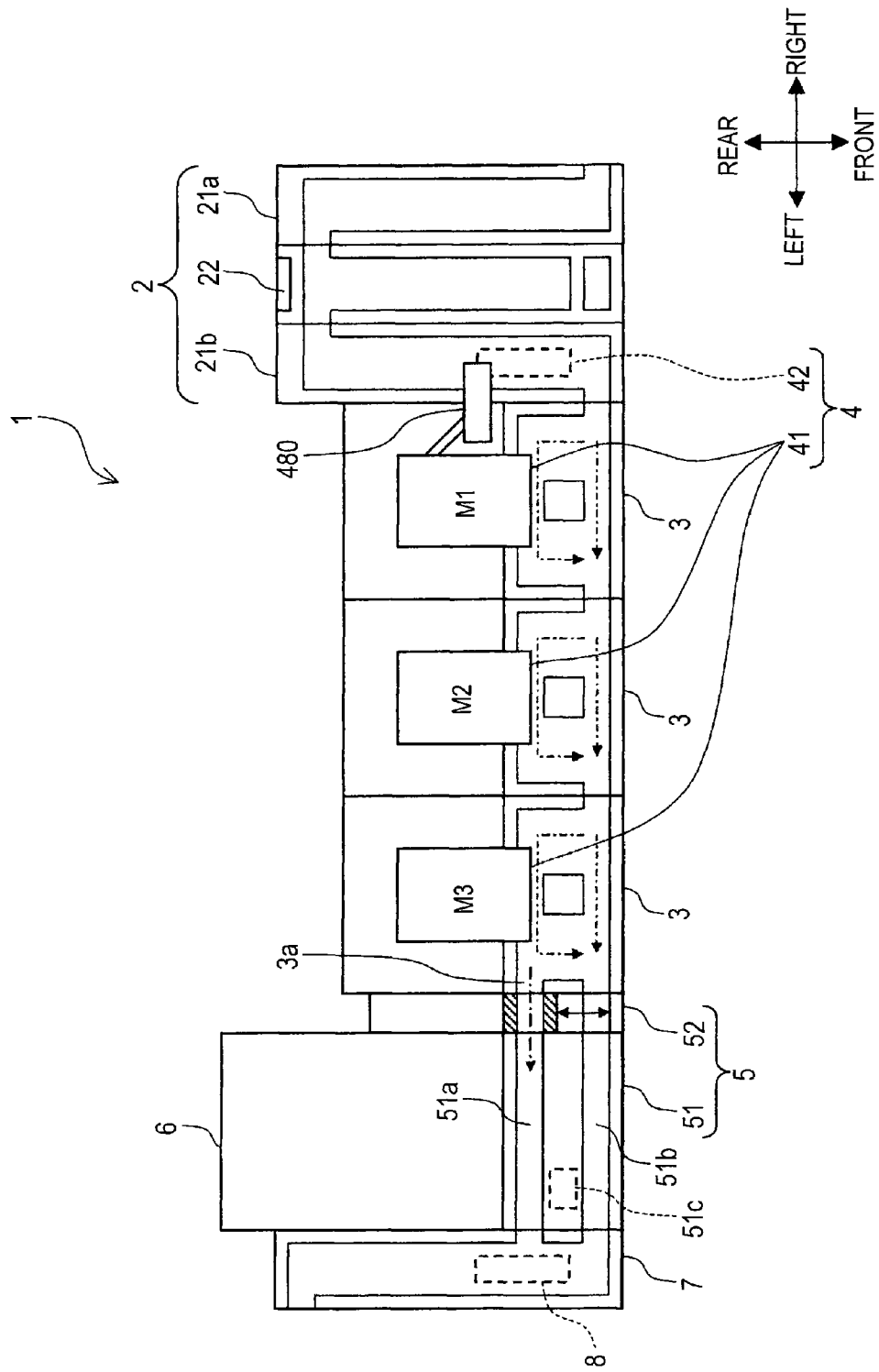
FIG. 13 is a diagram showing the configuration of a sample processing system according to a modified embodiment.

As shown in FIG. 13, a notch 3*a* may be provided in the sample transport apparatus 3 in front of M3. Accordingly, when a sample re-examined in M3 is further subjected to the preparation of a smear, the rack slider 52 may be positioned at the position of FIG. 13 so as to send the sample rack L to the rack transport passage 51*a* via the notch 3*a*.

In the above-described three embodiments, the inactive state is a state in which the supply of electric power to the pneumatic pressure source is stopped. However, the supply of electric power to another constituent section may be stopped or decreased. As the other constituent section, a warming mechanism or the like for warming a sample, reagent and the like, a cooling mechanism for cooling a sample, reagent and the like, is exemplified. For example, when a warming mechanism is used, in an inactive state, electric power may be supplied such that the heater has a predetermined temperature lower than a temperature at the time of warming, and in addition, when the determination result showing that an additional process is required is obtained, the supply amount of electric power may be increased such that the heater has a temperature at the time of warming. In this manner, while cutting power consumption, the interruption of the sample process occurring waiting for the heater to warm up can be avoided. As the heater, a rubber heater can be used. Since the power consumption of the rubber heater is large, the effect of the present invention is particularly large.

In the above-described three embodiments, the inactive state is a state in which the supply of electric power to the pneumatic pressure source is stopped. However, the inactive state may be a state that the supply of electric power to the entire measuring unit or the entire smear preparation apparatus is stopped, that is, a state that the measuring unit or the smear preparation apparatus is powered-off. A transition process to a power-off state of the measuring unit or the smear preparation apparatus may be automatically executed when a predetermined time has elapsed after operation situations was monitored and a predetermined condition was met as in the above-described three embodiments, or may be executed in response to the operation of a power switch by a user of the sample processing system. The transition to an inactive state by a user also can be executed in response to a power-off instruction input to the information processing apparatus in place of the power switch.

In the case where the inactive state is a state in which the measuring unit or the smear preparation apparatus is powered-off, the release of the inactive state is executed when the measuring unit or the smear preparation apparatus is started and enters a state (standby state) in which the measurement or the preparation of a smear can be performed.

In the case where the inactive state is a state in which the measuring unit or the smear preparation apparatus is powered-off, the power consumption cutting effect is larger than in the case where the electric power supply is partially stopped, as in the case where only the supply of electric power to the pneumatic pressure source is stopped.

In addition, in the above-described three embodiments, the measuring unit or the smear preparation apparatus is shifted to an inactive state. However, the sample transport apparatus in front of the measuring unit M3 or the sample transport apparatus in front of the smear preparation apparatus may be shifted to an inactive state. Regarding shifting of the sample transport apparatus to an inactive state and the release of an inactive state, as in the case of the measuring unit or the smear preparation apparatus, the transition to an inactive state may be carried out when a predetermined period of time elapses after a predetermined condition has been met, and the inactive state may be released when the determination result showing that an additional process is required is obtained.

Arbitrarily, the embodiments of the present invention may be variously modified in the scope of the technical idea shown in the claims.

What is claimed is:

1. A sample processing system comprising:
    a sample transporting device having a plurality of conveying paths and configured to transport a sample rack on which one or more sample containers are set;
    at least one first module arranged along a first conveying path and configured to test a sample contained in a sample container set on the sample rack conveyed by the sample transporting device and to out output a test result, wherein the sample is blood or urine;
    at least one second module arranged along a second conveying path and configured to process the sample, which has been tested by the at least one first module, contained in the sample container set on the sample rack conveyed by the sample transporting device, wherein the at least one second module comprises a sample preparation section configured to prepare a measurement sample from the sample contained in the sample container, a detector configured to measure the measurement sample supplied from the sample preparation section and a pneumatic pressure source configured to supply a pressure for transporting the measurement sample to the detector from the sample preparation section and is switchable between an active state and an inactive state by switching whether to supply electricity to the pneumatic pressure source;
    a sample storage device receiving the sample rack from the sample transporting device and storing the received sample rack; and
    at least one processor and at least one memory that stores programs executable collectively by the at least one processor, wherein the at least one processor performs operations comprising:
    monitoring activities for processing of the respective at least one second module;
    halting a supply of electricity to the pneumatic pressure source in response to a predetermined elapsed time from a last activity of the at least one second module for processing,
    obtaining a determination result as to whether a sample which has been tested by the at least one first module is necessary to be processed by the at least one second module;
    if the sample is necessary to be processed by the at least one second module as the determination result, starting transportation of a sample container containing the sample to the at least one second module for processing, and
    resuming the supply of electricity to the pneumatic pressure source to make the at least one second module ready to process the sample, in response to arrival of the sample container to the second conveying path; and
    if the sample is not necessary to be processed by the at least one second module as the determination result, transporting the sample container containing the sample to the sample storage device through a third conveying path other than the first and second conveying paths, and keeping the halt of the supply of electricity to the pneumatic pressure source of the at least one second module.

2. The sample processing system according to claim 1, wherein the at least one processor performs the monitoring by monitoring sensors arranged along the second conveying path for detecting the sample on the second conveying path.

3. The sample processing system according to claim 2, wherein the second conveying path comprises a roundabout path for the at least one second module in order to load a sample onto the at least one second module, and the at least one processor monitors sensors arranged along the roundabout path for the at least one second module.

4. A sample processing system comprising,
a sample transporting device having a plurality of conveying paths and configured to transport a sample rack on which one or more sample containers are set;
at least one first module arranged along a first conveying path and configured to test a sample contained in a sample container set on the sample rack conveyed by the sample transporting device and to out output a test result;
at least one second module arranged along a second conveying path and configured to process the sample, which has been tested by the at least one first module, contained in the sample container set on the sample rack conveyed by the sample transporting device, wherein the at least one second module is a smear preparation apparatus comprising a specimen preparation section configured to prepare a smear and a pneumatic pressure source configured to supply a pressure for fluid feeding to the specimen preparation section and is switchable between an active state and an inactive state by switching whether to supply electricity to the pneumatic pressure source;
a sample storage device receiving the sample rack from the sample transporting device and storing the received sample rack; and
at least one processor and at least one memory that stores programs executable collectively by the at least one processor, wherein the at least one processor performs operations comprising:
monitoring activities for processing of the smear preparation apparatus;
halting a supply of electricity to the pneumatic pressure source in response to a predetermined elapsed time from a last activity of the smear preparation apparatus for preparing a smear,
obtaining a determination result as to whether a sample which has been tested by the at least one first module is necessary to be processed by the smear preparation apparatus;
if the sample is necessary to be processed by the smear preparation apparatus as the determination result, starting transportation of a sample container containing the sample to the smear preparation apparatus, and
resuming the supply of electricity to the pneumatic pressure source to make the smear preparation apparatus ready to prepare the smear from the sample, in response to arrival of the sample container to the second conveying path; and
if the sample is not necessary to be processed by the smear preparation apparatus as the determination result, transporting the sample container containing the sample to the sample storage device through a third conveying path other than the first and second conveying paths, and keeping the halt of the supply of electricity to the pneumatic pressure source of the smear preparation apparatus.

5. The sample processing system according to claim 1, wherein the sample is blood and the first and second module analyze blood cells in the blood.

6. The sample processing system according to claim 1, wherein the first module conducts an initial testing of the sample, and the second module conducts a re-testing of the sample.

7. The sample processing system according to claim 1, wherein the at least one processor waits for the at least one second module to come in the active by resuming the supply of electricity to the pneumatic pressure source before instructing the at least one second module to initiate processing of the sample.

8. The sample processing system according to claim 1, wherein the at least one processor prohibits halting the supply of electricity to the pneumatic pressure source of the at least one second module if the sample is determined necessary to be processed by the at least one second module.

9. The sample processing system according to claim 1, wherein the at least one processor resumes the supply of electricity to the pneumatic pressure source to make the at least one second module ready to process the sample a predetermined time after obtaining the determination result.

10. The sample processing system according to claim 1, wherein the at least one processor is connected to a host computer via a communication network, wherein the host computer determines whether the sample which has been tested by the at least one first module is necessary to be processed by the at least one second module, and the at least one processor obtains the determination result from the host computer.

11. The sample processing system according to claim 1, wherein the at least one processor receives the test result output by the at least one first module, and determines whether a sample which has been tested by the at least one first module is necessary to be processed by the at least one second module, based on the test result.

12. A method for saving electricity consumed by a sample processing system, the method comprising steps of:
monitoring activities for processing of respective at least one second module configured to process a sample which has been tested by at least one first module configured to test the sample and to output a test result, wherein the sample is blood or urine, wherein the at least one second module comprises a sample preparation section configured to prepare a measurement sample from the sample contained in the sample container, a detector configured to measure the measurement sample supplied from the sample preparation section and a pneumatic pressure source configured to supply a pressure for processing the sample and is switchable between an active state and an inactive state by switching whether to supply electricity to the pneumatic pressure source;
halting a supply of electricity to the pneumatic pressure source in response to a predetermined elapsed time from a last activity of the at least one second module for processing,
transporting a sample to the at least one first module through a first path;
obtaining, based on the test result output by the at least one first module, a determination result as to whether a sample which has been tested by the at least one first module is necessary to be processed by the at least one second module,
if the sample is necessary to be processed by the at least one second module as the determination result, transporting the sample to the at least one second module through a second path; and
resuming the supply of electricity to the pneumatic pressure source placing to make the at least one second module ready to process the sample, in response to arrival of the sample container to the second path; and
if the sample is not necessary to be processed by the at least one second module as the determination result, transporting the sample to a storage device through a third path other than the first and second paths, and keeping the halt of the supply of electricity to the pneumatic pressure source of the at least one second module.

13. The method according to claim 12, wherein the at least one second module is a smear preparation apparatus or a sample testing apparatus for a re-testing of the sample.

14. A non-transitory storage medium which stores programs executable collectively by at least one processor of a sample processing system, the at least one processor performing operations comprising:
monitoring activities for processing of respective at least one second module configured to process a sample which has been tested by at least one first module configured to test the sample and to out output a test result, wherein the sample is blood or urine, wherein the at least one second module comprises a sample preparation section configured to prepare a measurement sample from the sample contained in the sample container, a detector configured to measure the measurement sample supplied from the sample preparation section and a pneumatic pressure source configured to supply a pressure for processing the sample and is switchable between an active state and an inactive state by switching whether to supply electricity to the pneumatic pressure source;
halting a supply of electricity to the pneumatic pressure source in response to a predetermined elapsed time from a last activity of the at least one second module for processing,
transporting a sample to the at least one first module through a first path;
obtaining, based on the test result output by the at least one first module, a determination result as to whether a sample which has been tested by the at least one first module is necessary to be processed by the at least one second module,
if the sample is necessary to be processed by the at least one second module as the determination result, transporting the sample to the at least one second module through a second path, and resuming the supply of electricity to the pneumatic pressure source to make the at least one second module ready to process the sample, in response to arrival of the sample container to the second path; and
if the sample is not necessary to be processed by the at least one second module as the determination result, transporting the sample to a sample storage device through a third path other than the first and second paths, and keeping the halt of the supply of electricity to the pneumatic pressure source.

15. The sample processing system according to claim 1, wherein the sample transporting device comprises a first transport device having the first conveying path, a fourth conveying path, a first pre-analysis rack holding section and a first post-analysis rack holding section, and a second transport device having the second conveying path, the third conveying path, a second pre-analysis rack holding section and a second post-analysis rack holding section, wherein the fourth conveying path is connected to the third conveying path, the first pre-analysis rack holding section and the first post-analysis rack holding section are arranged between the first conveying path and the fourth conveying path, and the second pre-analysis rack holding section and the second post-analysis rack holding section are arranged between the second conveying path and the third conveying path.

16. The sample processing system according to claim 1, wherein the detector comprises a flow cytometer.

17. The sample processing system according to claim 1, wherein the sample is urine and the first and second module analyze urine.

18. The method according to claim 12, wherein the sample is urine and the first and second module analyze urine.

* * * * *